US008658395B2

(12) United States Patent
Zhang et al.

(10) Patent No.: US 8,658,395 B2
(45) Date of Patent: *Feb. 25, 2014

(54) SELECTIVE INCORPORATION OF 5-HYDROXYTRYPTOPHAN INTO PROTEINS IN MAMMALIAN CELLS

(75) Inventors: Zhiwen Zhang, San Diego, CA (US); Lital Alfonta, San Diego, CA (US); Peter G. Schultz, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/546,582

(22) Filed: Jul. 11, 2012

(65) Prior Publication Data

US 2012/0282626 A1 Nov. 8, 2012

Related U.S. Application Data

(60) Continuation of application No. 12/798,979, filed on Apr. 14, 2010, now Pat. No. 8,242,244, which is a division of application No. 10/580,987, filed as application No. PCT/US2004/042535 on Dec. 16, 2004, now Pat. No. 7,741,071.

(60) Provisional application No. 60/548,761, filed on Feb. 26, 2004, provisional application No. 60/531,312, filed on Dec. 18, 2003.

(51) Int. Cl.
*C12P 21/06* (2006.01)
*C12N 9/00* (2006.01)
*C12N 15/74* (2006.01)

(52) U.S. Cl.
USPC .......................... 435/69.1; 435/183; 435/471

(58) Field of Classification Search
USPC ........................................ 435/69.1, 183, 471
See application file for complete search history.

(56) References Cited

U.S. PATENT DOCUMENTS

| 7,045,337 B2 | 5/2006 | Schultz et al. |
| 2003/0082575 A1 | 5/2003 | Schultz et al. |
| 2003/0108885 A1 | 6/2003 | Schultz et al. |

OTHER PUBLICATIONS

Humphries et al., Journal of Electroanalytical Chemistry vol. 346, Issues 1-2, Mar. 10, 1993, pp. 377-403. Abstract.*
Agren et al., 1991 Low brain uptake of L-[11C]5-hydroxytryptophan in major depression: a positron emission tomography study on patients and healthy volunteersActa Psychiatrica Scandinavica, pp. 449-455; Abstract.*
5-Hydroxytryptophan From Wikipedia, the free encyclopedia Jun. 13, 2013.*
A. K. Kowal, et al "Twenty-first aminoacyl-tRNA synthetase-suppressor tRNA pairs for possible use in site-specific incorporation of amino acid analogues into proteins in eukaryotes and in eubacteria", Proc. Natl. Acad. Sci. USA 98, 2268-2273 (2001).
Biochemistry (1990) John Wiley and Sons, pp. 126-128.
Chin et al. (2003) "An Expanded Eukaryotic Genetic Code." *Science*, 301: 964-967.
Chow et al., "Cloning and Nucleotide Sequence of the Structural Gene Coding for *Bacillus subtilis* Tryptophanyl-tRNA Synthetase," Gene, vol. 73, pp. 537-543 (1988).
Chow et al., "Mutational Identification of an Essential Tryptophan in Tryptophanyl-tRNA Synthetase of *Bacillus subtillis*", J. Biol. Chem., 267(13):9146-9149 (1992).
Cusack (1997) "Aminoacyl-tRNA Synthetases," Current Opinion in Structural Biology, pp. 881-889.
Deiters et al. (2003) "Adding Amino Acids with Novel Reactivity to the Genetic Code of *Saccharomyces cerevisiae*." *Journal of the American Chemistry Society*,125(39): 11782-11783.
Guo et al. (2004) "Protein Tolerance to Random Amino Acid Change." *Proceedings of the National Academy of Sciences*, USA, 101(25): 9205-9210.
Houge et al., "Characterization of Aminoacyl-Adenylates in *B. subtilis* Tryptophanyl-tRNA Synthetase, by the Fluorescence of Tryptophan Analogs 5-Hydroxytryptophan and 7-Azatryptophan," *Biophysical Chemistry*, vol. 48, pp. 159-169 (1993).
Ibba, "The Renaissance of Aminoacyl-tRNA Synthesis," EMBO reports, vol. 21, No. 51, pp. 382-387, (2001).
Kimchi-Sarfaty et al. (2007) "A 'silent' Polymorphism in the MDR1 Gene Changes Substrate Specificity." *Science*, 26(315): 525.
Koher et al., "Import of Amber and Ochre Suppressor tRNAs into Mammalian Cells: A General Approach to Site-Specific Insertion of Amino Acid Analogues into Proteins," PNAS, vol. 98, No. 25, pp. 14310-14315, (2001).
Liu and Schultz (1999) "Progress toward the evolution of an organism with an expanded genetic code." *Proceedings of the National Academy of Sciences*, USA, 96: 4780-4785.
Marti-Renom et al. (2000) "Comparative Protein Structure Modeling of Genes and Genomes." *Ann Rev. Biophys. Biomed. Struct.*, 29: 291-325.
Pastrnak et al. (2000) "A New Orthogonal Suppressor tRNA/ Aminoacyl-tRNA Synthetase Pair for Evolving an Organism with an Expanded Genetic Code." *Helevetica Chimica Acta*. 83: 2277-2286.
Sakamoto et al., "Site-specific Incorporation of an Unnatural Amino Acid into Proteins in Mammalian Cells", N. A. Res., vol. 30, No. 21 4692-4699, (2002).
Skolnick et al. (2000) "From genes to protein structure and function: novel applications of computational approaches in the genomic era." *Tibtech*, 18: 34-39.
Ulmasov et al. (1998) "Identity elements and aminoacylation of plant tRNA$^{Trp}$." *Nucleic Acids Research*, 26(22): 5139-5141.
Wang et al., "A General Approach for the Generation of Orthogonal tRNAs," Chem. & Bio., pp. 883-890, (2001).

* cited by examiner

*Primary Examiner* — Maria Leavitt
(74) *Attorney, Agent, or Firm* — Quine Intellectual Property Law Group, P.C.

(57) ABSTRACT

This invention provides methods and compositions for incorporation of an unnatural amino acid into a peptide using an orthogonal aminoacyl tRNA synthetase/tRNA pair. In particular, an orthogonal pair is provided to incorporate 5-hydroxy-L-tryptophan in a position encoded by an opal mutation.

7 Claims, 5 Drawing Sheets

SEQUENCE LISTING

<160> NUMBER OF SEQ ID NOS: 7

<210> SEQ ID NO 1
<211> LENGTH: 993
<212> TYPE: DNA
<213> ORGANISM: Artificial
<220> FEATURE:
<223> OTHER INFORMATION: encodes Val144Pro mutant of Bacillus subtilis
      tryptophanyl-tRNA synthetase

<400> SEQUENCE: 1

```
atgaaacaaa cgattttttc aggcattcag ccaagcggct cagtgacgct cggcaactat     60
atcggtgcaa tgaagcagtt tgtcgaactg cagcatgatt ataacagcta ttttgcatc    120 gtcgatcagc atgcgataac tgttcctcaa gaccggcttg agcttagaaa gaatatccgc    180
aatctcgcgg cgctttactt agctgtcgga cttgatccag aaaaagcaac attgtttatt    240
cagtcagagg tccccgcaca tgcgcaggcc ggatggatga tgcagtgtgt cgcctatatc    300
ggcgagcttg agcggatgac tcaatttaag gacaaatcca aaggcaatga agctgtcgtc    360
tccggcctgt taacatatcc gccgctgatg ccgctgata ttctgctgta cggaacggat    420
cttgtacctc ccggcgagga tcaaaagcag caccttgagc tgacgcggaa tcttgcagaa    480
cgcttcaaca aaaatacaa cgacatcttt acgattccgg aagtgaaaat tccaaaagtc    540
ggtgcacgta tcatgtctct gaatgatccg ctgaagaaaa tgagcaaatc tgatccgaat    600
cagaaagctt atattacatt gctggatgag ccgaagcagc ttgaaaagaa atcaaaagc    660 gcagtaacgg attctgaagg cattgtcaaa tttgataagg aaaacaaacc gggcgtttcc    720
aaccttctta caattttattc aatcctcggc aatacgacaa ttgaagagct tgaagcaaag    780
tacgaaggaa aaggctacgg cgagtttaaa ggtgatttgg cagaagtcgt agtgaacgca    840
ttaaaaccga tccaggaccg ctattacgag ctgatagaat ctgaagaatt agaccggatt    900
cttgatgaag gcgcggaacg agcgaatcgg acagcaaaca aaatgctgaa aaaaatggag    960
aatgccatgg gtcttggaag aaaaagacgc taa                                  993
```

<210> SEQ ID NO 2
<211> LENGTH: 330
<212> TYPE: PRT
<213> ORGANISM: Artificial
<220> FEATURE:
<223> OTHER INFORMATION: Val144Pro mutant of Bacillus subtilis
      tryptophanyl-tRNA synthetase

<400> SEQUENCE: 2

```
Met Lys Gln Thr Ile Phe Ser Gly Ile Gln Pro Ser Gly Ser Val Thr
  1               5                  10                  15

Leu Gly Asn Tyr Ile Gly Ala Met Lys Gln Phe Val Glu Leu Gln His
                 20                  25                  30

Asp Tyr Asn Ser Tyr Phe Cys Ile Val Asp Gln His Ala Ile Thr Val
             35                  40                  45

Pro Gln Asp Arg Leu Glu Leu Arg Lys Asn Ile Arg Asn Leu Ala Ala
         50                  55                  60

Leu Tyr Leu Ala Val Gly Leu Asp Pro Glu Lys Ala Thr Leu Phe Ile
 65                  70                  75                  80

Gln Ser Glu Val Pro Ala His Ala Gln Ala Gly Trp Met Met Gln Cys
                 85                  90                  95

Val Ala Tyr Ile Gly Glu Leu Glu Arg Met Thr Gln Phe Lys Asp Lys
                100                 105                 110
```

```
Ser Lys Gly Asn Glu Ala Val Val Ser Gly Leu Leu Thr Tyr Pro Pro
        115                 120                 125

Leu Met Ala Ala Asp Ile Leu Leu Tyr Gly Thr Asp Leu Val Pro Pro
    130                 135                 140

Gly Glu Asp Gln Lys Gln His Leu Glu Leu Thr Arg Asn Leu Ala Glu
145                 150                 155                 160

Arg Phe Asn Lys Lys Tyr Asn Asp Ile Phe Thr Ile Pro Glu Val Lys
                165                 170                 175

Ile Pro Lys Val Gly Ala Arg Ile Met Ser Leu Asn Asp Pro Leu Lys
            180                 185                 190

Lys Met Ser Lys Ser Asp Pro Asn Gln Lys Ala Tyr Ile Thr Leu Leu
        195                 200                 205

Asp Glu Pro Lys Gln Leu Glu Lys Lys Ile Lys Ser Ala Val Thr Asp
    210                 215                 220

Ser Glu Gly Ile Val Lys Phe Asp Lys Glu Asn Lys Pro Gly Val Ser
225                 230                 235                 240

Asn Leu Leu Thr Ile Tyr Ser Ile Leu Gly Asn Thr Thr Ile Glu Glu
                245                 250                 255

Leu Glu Ala Lys Tyr Glu Gly Lys Gly Tyr Gly Glu Phe Lys Gly Asp
            260                 265                 270

Leu Ala Glu Val Val Val Asn Ala Leu Lys Pro Ile Gln Asp Arg Tyr
        275                 280                 285

Tyr Glu Leu Ile Glu Ser Glu Glu Leu Asp Arg Ile Leu Asp Glu Gly
    290                 295                 300

Ala Glu Arg Ala Asn Arg Thr Ala Asn Lys Met Leu Lys Lys Met Glu
305                 310                 315                 320

Asn Ala Met Gly Leu Gly Arg Lys Arg Arg
                325                 330

<210> SEQ ID NO 3
<211> LENGTH: 71
<212> TYPE: RNA
<213> ORGANISM: Artificial
<220> FEATURE:
<223> OTHER INFORMATION: mutant opal supressor tRNA

<400> SEQUENCE: 3
aggggcgugg cuuaacggua gagcagaggu cuucaaaacc uccggugugg guucgauucc      60
uaccgccccu g                                                         71

<210> SEQ ID NO 4
<211> LENGTH: 74
<212> TYPE: RNA
<213> ORGANISM: Bacillus subtilis

<400> SEQUENCE: 4
aggggcauag uuuaacggua gaacagaggu cuccaaaacc uccggugugg guucgauucc      60
uacugccccu gcca                                                       74

<210> SEQ ID NO 5
<211> LENGTH: 48
<212> TYPE: DNA
<213> ORGANISM: Arabidopsis sp.

<400> SEQUENCE: 5
aaaattaatt aaacgtttag aaatatatag atgaacttta tagtacaa                  48
```

```
<210> SEQ ID NO 6
<211> LENGTH: 12
<212> TYPE: DNA
<213> ORGANISM: Arabidopsis sp.

<400> SEQUENCE: 6 gtccttttt tg                                                          12

<210> SEQ ID NO 7
<211> LENGTH: 23
<212> TYPE: DNA
<213> ORGANISM: Artificial
<220> FEATURE:
<223> OTHER INFORMATION: oligonucleotide probe

<400> SEQUENCE: 7
cggaggtttt gaagacctct gct                                             23
```

SELECTIVE INCORPORATION OF 5-HYDROXYTRYPTOPHAN INTO PROTEINS IN MAMMALIAN CELLS

CROSS-REFERENCE TO RELATED APPLICATIONS

This application is a Continuation application claiming priority to and benefit of application Ser. No. 12/798,979, filed Apr. 14, 2010 (now U.S. Pat. No. 8,242,244), which is a Divisional application claiming priority to and benefit of a prior parent U.S. National phase application Ser. No. 10/580, 987, "Selective Incorporation of 5-Hyroxytryptophan into Proteins in Mammalian Cells" by Zhang, et al., filed under 35 U.S.C. §371 on May 25, 2006 (now U.S. Pat. No. 7,741,071); which claims benefit and priority from, Patent Cooperation Treaty application PCT/US04/042535, with an international filing date of Dec. 16, 2004; which claims priority to and benefit of a prior U.S. Provisional Application No. 60/548, 761, "Selective Incorporation of 5-Hydroxytryptophan into Proteins in Mammalian Cells", by Zhang, et al., filed Feb. 26, 2004; and, a prior U.S. Provisional Application No. 60/531, 312, "Selective Incorporation of 5-Hydroxytryptophan into Proteins in Mammalian Cells", by Zhang, et al., filed Dec. 18, 2003; each of which is incorporated herein by reference.

STATEMENT AS TO RIGHTS TO INVENTIONS MADE UNDER FEDERALLY SPONSORED RESEARCH AND DEVELOPMENT

This invention was made with Government support under Contract Number DE-FG03-00ER45812 awarded by the Department of Energy, and Contract Number NIH GM066494 awarded by the National Institutes of Health. Therefore, the United States government has certain rights in this invention.

FIELD OF THE INVENTION

The invention is in the field of protein expression. For example, compositions and methods for orthogonal expression of proteins including unnatural amino acid residues are provided.

BACKGROUND OF THE INVENTION

Proteins are the main building blocks and catalysts in life systems. Manipulation of genes through recombinant nucleic acid technologies, and expression of natural and engineered proteins, have provided many of the benefits associated with the genetic engineering revolution. Protein engineering, including incorporation of unnatural amino acids into peptides, can provide further practical benefits from the life sciences.

Translation of peptides encoded by nucleic acid sequences is accomplished in life systems through the complex interaction of many translation system constituent components, such as, e.g., ribosomes, mRNA, tRNAs, aminoacyl-tRNA synthetases, and amino acids. A strict set of rules and reliable reactions provide remarkably consistent translation of proteins by endogenous translation systems in living cells. A family of RNA polymerases first generates ribosomal RNA (rRNA), tRNAs, and mRNAs by transcription of DNA sequences. An endogenous family of aminoacyl-tRNA synthetases can each bind and link a specific amino acid (of the 20 natural amino acids) to a specific tRNA. Ribosomes, assembled from proteins and rRNA, align the unique anticodon of each tRNA with the complimentary codon presented in an mRNA chain to be translated. Finally, the ribosomes catalyze formation of a peptide bond between amino acids aligned together with their tRNAs along the mRNA chain. The ribosomes recognize a start codon (AUG-methionine) associated with a near by promoter sequence to determine a translation starting position and reading frame. Ribosomes generally respond to three mRNA termination codons (UAG, UGA, and UAA), not having associated tRNAs, as a signal to stop translation.

One way to provide proteins with unnatural side groups is to modify the protein after translation. Side groups of certain amino acids are chemically reactive and amenable to chemical modification. The sulfhydryl group of cysteine, hydroxyl group of tyrosine, and amino group of glutamine, e.g., can enter into reactions well known in the chemical arts, resulting in modifications or covalent bonding to side chains of amino acid residues. For example, lysine residue side chains, containing a epsilon-amino group, can be converted to acetyllysine by the enzymatic action of an acetyltransferase or by chemical reactions with, e.g., chemical acetylating agents, such as acetylacetate. However, post translational modifications are often non-specific and/or poorly directed.

Unnatural amino acids can also be incorporated into peptides by chemical synthesis. Automated chemical synthesis on a solid support matrix can provide a straightforward method to incorporate unnatural amino acids. However, routine solid-phase peptide synthesis is generally limited to small peptides or proteins with less than 100 residues. It is possible to make larger proteins with recently developed methods for enzymatic ligation or native chemical ligation of peptide fragments, but such methods are not easily scaled.

Unnatural amino acids can also be incorporated into proteins using mutant transcription system components. For example, orthogonal translation components can be added to native endogenous translation systems to translate peptides not normally provided by the endogenous translation system. In "An Engineered *Escherichia coli* Tyrosyl-tRNA Synthetase for Site-specific Incorporation of an Unnatural Amino Acid into Proteins in Eukaryotic Translation and Its Application in a Wheat Germ Cell-free System", by A. K. Kowal, et al., Proc. Natl. Acad. Sci. USA 98, 2268-73 (2001), tyrosyl-tRNA synthetase (TyrRS) from *Escherichia coli* was engineered to preferentially recognize 3-iodo-L-tyrosine rather than L-tyrosine for the site-specific incorporation of 3-iodo-L-tyrosine into proteins in eukaryotic in vitro translation systems. A similar translation system has been engineered to incorporate unnatural tyrosine analogs in a mammalian system. In "Site-specific Incorporation of an Unnatural Amino Acid into Proteins in Mammalian Cells", by K. Sakamoto, N. A. Res., Vol. 30, No. 21 4692-4699, (2002), an *E. Coli* TyrRS construct was expressed along with an *Bacillus stearothermophilus* amber suppressor t-RNA in mammalian cells to provide a ras protein having an iodo-tyrosine residue encoded by a TAG codon. The system was specific to iodo-tyrosine incorporation, and failed to describe useful unique properties of the translated peptides.

In view of the above, a need exists for improved methods to specifically incorporate unnatural amino acid residues into peptides at desired positions using eukaryotic translation systems. It would be desirable to have a way to incorporate unnatural residues other than halogenated tyrosine residues to peptides. Benefits could also be realized through incorporation of unnatural amino acids that are detectable without tags. Methods for incorporation of unnatural amino acids having specifically reactive chemical linkage groups would be useful in the diagnostic, therapeutic and materials sciences. The present invention provides these and other features that will be apparent upon review of the following.

SUMMARY OF THE INVENTION

The present invention includes compositions and methods to incorporate amino acids into atypical positions in a growing polypeptide chain. The compositions include, e.g., members of orthogonal aminoacyl-tRNA synthetase/orthogonal tRNA (O-RS/O-tRNA) pairs capable of incorporating amino acids, such as, e.g., 5-hydroxy-L-tryptophan (5-HTPP) into a position encoded by a selector codon. The invention includes mammalian cells with orthogonal pairs for incorporation of unnatural amino acids in vivo. The methods of the invention include, e.g., preparing orthogonal pair constructs for expression of the orthogonal pair in a translation system in which the O-RS charges the O-tRNA with an amino acid for incorporation into a peptide.

Compositions of the invention typically include: a translation system; an orthogonal aminoacyl-tRNA synthetase (O-RS), such as an orthogonal tryptophanyl-tRNA synthetase (O-TrpRS); an orthogonal mutant tryptophanyl-tRNA synthetase (O-muTrpRS), or a derivative thereof; and, an orthogonal tRNA (O-tRNA); so that the O-RS preferentially aminoacylates the O-tRNA with an amino acid or unnatural amino acid. The translation system can include, e.g., an in vitro translation system, or a cell, e.g., such as, e.g., a eukaryotic cell, a *Xenopus* cell, or a mammalian cell. In vitro translation typically includes a translation system with a cell lysate component. In a preferred embodiment, the composition comprises an orthogonal aminoacyl-tRNA synthetase (O-RS) that preferentially aminoacylates a tRNA (optionally, an O-tRNA) with 5-hydroxy-L-tryptophan (5-HTPP).

The O-RS of the composition can include orthogonal aminoacyl-tRNA synthetases having improved or enhanced enzymatic properties, such as, e.g., an improved Km and/or Kcat for the unnatural amino acid over a natural amino acid. In a preferred embodiment, the O-RS can be encoded by a nucleic acid with the polynucleotide sequence of a *Bacillus subtilis* tryptophanyl-tRNA synthetase mutated to replace valine 144 with proline using the codon CCC, e.g., the nucleic acid sequence of Val144ProBsTrpRS (SEQ ID NO: 1), a conservative variation thereof, and/or a complementary polynucleotide sequence. In another preferred embodiment, the O-RS can have the amino acid sequence Val144ProBsTrpRS (SEQ ID NO: 2), and/or conservative substitutions thereof.

The O-tRNA can be preferentially aminoacylated by its cognate O-RS, while the O-tRNA is not substantially aminoacylated by an endogenous aminoacyl-tRNA synthetase of an endogenous translation system. In a preferred embodiment, O-tRNA can have the polynucleotide sequence of a mutant orthogonal opal suppressor tRNA, such as, e.g., mutRNA$_{UCA}^{Trp}$ (SEQ ID NO: 3), conservative variations thereof, and/or complementary polynucleotide sequences thereof. The O-tRNAs of the invention typically recognize a selector codon, such as, e.g., a four base codon, a rare codon, UUA, CUA, or UCA.

Orthogonal pairs, endogenous translation systems, unnatural amino acids, and the like, can be used to incorporate atypical amino acids into a product peptide. The product peptide can be encoded by, e.g., a nucleic acid having a selector codon sequence recognized by the O-tRNA. Many useful product peptides have an amino acid sequence that is at least 75% identical to that of a wild type therapeutic protein, a diagnostic protein, an industrial enzyme, or a portion thereof.

Compositions of the invention can include, e.g., an endogenous translation system of RSs, tRNAs, amino acids, mRNAs, rRNAs, and other components endogenous to a natural translation system, e.g., of a living organism, a cell or lysate of cells. Orthogonal components, such as, e.g., O-tRNAs, O-RSs, mRNAs with selector codons, and/or unnatural amino acids, can be added to endogenous translation systems to obtain unusual transcription products. The endogenous translation system can be native to a cell, a lysate, an in vitro translation system, or derived therefrom.

The present invention includes polypeptides with an amino acid sequence encoded by a coding polynucleotide sequence such as, e.g., a) a coding polynucleotide sequence from SEQ ID NO: 1, or a conservative variation thereof; b) a coding polynucleotide sequence that encodes a polypeptide of SEQ ID NO: 2, or conservative substitutions thereof; c) a polynucleotide sequence that hybridizes under highly stringent conditions over substantially the entire length of the polynucleotide sequences of (a) or (b); and/or, d) sequences complementary to any of (a), (b), or (c); wherein the polypeptide has aminoacyl-tRNA synthetase activity charging a tRNA with a tryptophan analog, such as 5-HTPP.

The present invention includes nucleic acids with sequences for tRNAs, such as, e.g.: a) the polynucleotide sequence of SEQ ID NO: 1, or its complement; b) conservative variations of (a) that recognizes a selector codon; and/or, c) a polynucleotide sequence which hybridizes under highly stringent conditions over substantially the entire length of polynucleotide sequence (a), and which comprises a tRNA that recognizes a selector codon, such as four base codon, UGA, UAA, and UAG.

In one aspect of the invention, a mammalian cell is capable of incorporating tryptophan analogs during translation of an mRNA. For example, a mammalian cell can incorporate an amino acid into a growing peptide using an orthogonal aminoacyl-tRNA synthetase (O-RS), such as an orthogonal tryptophanyl-tRNA synthetase (O-TrpRS), an orthogonal mutant tryptophanyl-tRNA synthetase (O-muTrpRS), and/or a derivative thereof; and using an orthogonal tRNA (O-tRNA) preferentially aminoacylated by the O-RS with the natural or unnatural amino acid. In certain embodiments, the O-RS is encoded by a nucleic acid having the polynucleotide sequence of SEQ ID NO: 1, a conservative variation thereof, or a complementary polynucleotide sequence. The O-RS can have, e.g., an amino acid sequence of SEQ ID NO: 2 or a conservatively substituted variation. In many cases, the O-tRNA is not substantially aminoacylated by any endogenous aminoacyl-tRNA synthetase of the cell. The O-tRNA can exist in the cell as, e.g., the polynucleotide sequence of SEQ ID NO: 3, a conservative variation thereof, or a complementary polynucleotide sequence. Typical unnatural amino acids that can be incorporated by the mammalian cell with orthogonal translation constituents include, e.g., tryptophan analogs and 5-hydroxy-L-tryptophan (5-HTPP).

The invention includes methods for incorporation of amino acids into peptides, typically, by provision of orthogonal translation system components into an endogenous translation system. For example, the methods can include preparing a construct comprising a nucleic acid sequence encoding an orthogonal mutant tryptophanyl-tRNA synthetase (O-muTrpRS) and/or a derivative thereof, preparing a construct comprising a nucleic acid sequence encoding an orthogonal tRNA (O-tRNA), transfecting a eukaryotic cell with the O-muTrpRS construct and the O-tRNA construct, and preferentially charging the expressed O-tRNA with the amino acid or unnatural amino acid using the expressed O-muTrpRS to incorporate the amino acid into the peptide in the cell.

In a preferred embodiment, the unnatural amino acid is 5-hydroxy-L-tryptophan (5-HTPP). Peptides incorporating 5-HTPP using methods of the invention can by employed in cross linking to other molecules, e.g., by applying a voltage to the peptide, to react the 5-HTPP with a reactive molecule, e.g., to cross-link the peptide with the reactive molecule. In one embodiment, the reactive molecule is another peptide with an incorporated unnatural amino acid, such as 5-HTPP. Peptides incorporating 5-HTPP can also be used to detect interactions between the peptide and another peptide, e.g., by fluoroscopy.

Methods of the invention, can be practiced, e.g., with O-muTrpRS constructs encoding tryptophanyl-tRNA synthetase peptide sequences mutated at one or more amino acid residues based on structure data of the tryptophanyl-tRNA synthetase or an analogous aminoacyl-tRNA synthetase. For example, the mutated tryptophanyl-tRNA synthetase can be a *Bacillus* tryptophanyl-tRNA synthetase mutated at a valine in the region at or near residue 144. In a preferred embodiment, the O-muTrpRS construct can be encoded by the polynucleotide sequence of: a) SEQ ID NO: 1 or a conservative variation, b) a polynucleotide sequence that encodes a polypeptide with the sequence of SEQ ID NO: 2 or a conservative substitution, c) a polynucleotide sequence which hybridizes under highly stringent conditions over substantially the entire length of a polynucleotide sequence of (a) or (b), or d) a complementary sequence of (a), (b), or (c).

O-tRNAs of the methods can be provided by expression of constructs adapted to function in an endogenous translation system. The O-tRNA construct can have the polynucleotide sequence of SEQ ID NO: 3, a conservative variation, or a complementary polynucleotide sequence thereof. The O-tRNA construct can include one or more tRNA flanking sequences that functionally interact with an RNA polymerase of a cell used as a translation system. For example, the O-tRNA construct can have an A box eukaryotic transcriptional control element, e.g., obtained by mutating a prokaryotic tRNA sequence to include the A box eukaryotic transcriptional control element. Such mutations can preferably be accomplished by site directed mutagenesis. Other useful O-tRNA construct elements include, e.g., a reporter tag or a purification tag. The O-tRNA construct can include an anticodon complimentary to an mRNA selector codon mRNA sequence encoding the peptide, to incorporate the unnatural amino acid into the peptide. More than one orthogonal translation component can be expressed from the same construct, e.g., with the O-muTrpRS and the O-tRNA sequences on the same construct.

Constructs can be introduced into living cells for expression in an in vivo translation system and/or extracted from a cell for incorporation into an in vitro translation system. Introducing, as used in the methods of the invention, includes any means to insert a construct into a living cell for replication and/or expression. In preferred embodiments, the constructs are transfected into a eukaryotic cell or mammalian cell. Expression products, such as, e.g., alloproteins, O-tRNAs, O-RSs, and the like, can remain crude, be partially purified, and/or highly purified, as desired.

DEFINITIONS

Unless otherwise defined herein or below in the remainder of the specification, all technical and scientific terms used herein have meanings commonly understood by those of ordinary skill in the art to which the present invention belongs.

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" can include plural referents unless the content clearly dictates otherwise. Thus, for example, reference to "a component" can include a combination of two or more components; reference to "an amino acid" can include mixtures of appropriate amino acids, and the like.

Although many methods and materials similar, modified, or equivalent to those described herein can be used in the practice of the present invention without undue experimentation, currently preferred materials and methods are described herein. In describing and claiming the present invention, the following terminology will be used in accordance with the definitions set out below.

An O-RS "preferentially aminoacylates" a cognate O-tRNA when the O-RS charges the O-tRNA with an amino acid more efficiently than it charges any endogenous tRNA in an expression system. That is, when the O-tRNA and any given endogenous tRNA are present in a translation system in approximately equal molar ratios, the O-RS will charge the O-tRNA more frequently than it will charge the endogenous tRNA. Preferably, the relative ratio of O-tRNA charged by the O-RS to endogenous tRNA charged by the O-RS is high, preferably resulting in the O-RS charging the O-tRNA exclusively, or nearly exclusively, when the O-tRNA and endogenous tRNA are present in equal molar concentrations in the translation system. The relative ratio between O-tRNA and endogenous tRNA that is charged by the O-RS, when the O-tRNA and O-RS are present at equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

The O-RS "preferentially aminoacylates an O-tRNA with an unnatural amino acid" when (a) the O-RS preferentially aminoacylates the O-tRNA compared to an endogenous tRNA, and (b) where that aminoacylation is specific for the unnatural amino acid, as compared to aminoacylation of the O-tRNA by the O-RS with any natural amino acid. That is, when the unnatural and natural amino acids are present in equal molar amounts in a translation system comprising the O-RS and O-tRNA, the O-RS will load the O-tRNA with the unnatural amino acid more frequently than with the natural amino acid. Preferably, the relative ratio of O-tRNA charged with the unnatural amino acid to O-tRNA charged with the natural amino acid is high. More preferably, O-RS charges the O-tRNA exclusively, or nearly exclusively, with the unnatural amino acid. The relative ratio between charging of the O-tRNA with the unnatural amino acid and charging of the O-tRNA with the natural amino acid, when both the natural and unnatural amino acids are present in the translation system in equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

As used herein, an orthogonal tryptophanyl-tRNA (trp-O-tRNA) is a tRNA that is orthogonal to a translation system of interest, where the tRNA is: (1) identical or substantially similar to a naturally occurring trp-tRNA, (2) derived from a naturally occurring trp-tRNA by natural or artificial mutagenesis, (3) derived by any process that takes a sequence of a wild-type or mutant trp-tRNA sequence of (1) or (2) into account, (4) homologous to a wild-type or mutant trp-tRNA; (5) homologous to any example tRNA that is designated as a substrate for a Val144ProBsTrpRS (SEQ ID No.: 2), or (6) a conservative variant of any example tRNA that is designated as a substrate for Val144ProBsTrpRS. The trp-tRNA can exist charged with an amino acid, or in an uncharged state. It is also to be understood that a "trp-O-tRNA" optionally is charged (aminoacylated) by a cognate synthetase with an amino acid other than tryptophan, e.g., with the amino acid HTPP. Indeed, it will be appreciated that a trp-O-tRNA of the invention is advantageously used to insert essentially any amino acid, whether natural or artificial, into a growing polypeptide, during translation, in response to a selector codon.

As used herein, an orthogonal tryptophanyl-tRNA synthetase (O-TrpRS) is an enzyme that preferentially aminoacylates an O-tRNA (such as, e.g., an trp-O-tRNA) with an amino acid in a translation system of interest. The amino acid that the O-TrpRS loads onto the O-tRNA can be any amino acid, whether natural or artificial, and is not limited herein. The synthetase is optionally the same as, or homologous to, a naturally occurring tryptophanyl amino acid synthetase, or the same as or homologous to Val144ProBsTrpRS. For example, the O-TrpRS can be a conservative variant of peptide SEQ ID No.: 2, the peptide encoded by nucleic acid SEQ ID No.: 1, and/or can be at least 50%, 60%, 70%, 80%, 90%, 95%, 98%, 99% or more identical in sequence to an O-RS of SEQ ID.: 2 or encoded by SEQ ID No.: 1.

The term "selector codon" refers to codons recognized by an O-tRNA in a translation system and not recognized to a significant degree by an endogenous tRNA of the translation system. The O-tRNA anticodon loop can recognize the selector codon on the mRNA for incorporation of its amino acid (e.g., a preferentially aminoacylated unnatural amino acid) into a peptide at a position encoded by the selector codon. Selector codons can include, e.g., nonsense codons, such as stop codons, e.g., amber, ochre, and opal codons; four or more base codons; codons derived from natural or unnatural bases, and the like. For a given system, a selector codon can also include one of the natural three base codons, wherein the endogenous components of the translation system do not efficiently use the natural three base codon, e.g., a system that is lacking a tRNA that recognizes the natural three base codon or a system wherein the natural three base codon is a rare codon.

As used herein, the term "orthogonal" refers to a molecule (e.g., an orthogonal tRNA (O-tRNA) and/or an orthogonal aminoacyl tRNA synthetase (O-RS)) that functions with endogenous components of a cell or translation system with reduced efficiency as compared to a corresponding molecule that is endogenous to the cell or translation system, or that fails to function when paired with endogenous components of the cell. In the context of tRNAs and aminoacyl-tRNA synthetases, orthogonal refers to an inability or reduced efficiency (e.g., less than 20% efficiency, less than 10% efficiency, less than 5% efficiency, or less than 1% efficiency), of an orthogonal tRNA to function with an endogenous tRNA synthetase compared to the ability of an appropriate (e.g., homologous or analogous) endogenous tRNA to function when paired with the endogenous complimentary tRNA synthetase; or of an orthogonal aminoacyl-tRNA synthetase to function with an endogenous tRNA compared to the ability of an appropriate endogenous tRNA synthetase to function when paired with the endogenous complimentary tRNA. The orthogonal molecule lacks a functionally normal endogenous complementary molecule in the cell. For example, an orthogonal tRNA in a cell is aminoacylated by any endogenous RS of the cell with reduced or even undetectable efficiency, when compared to aminoacylation of an endogenous tRNA by the endogenous RS. In another example, an orthogonal RS aminoacylates any endogenous tRNA in a cell of interest with reduced or even undetectable efficiency, as compared to aminoacylation of the endogenous tRNA by a complimentary endogenous RS. A second orthogonal molecule can be introduced into the cell that functions when paired with the first orthogonal molecule. For example, an orthogonal tRNA/RS pair includes introduced complementary components that function together in the cell with an efficiency (e.g., 45% efficiency, 50% efficiency, 60% efficiency, 70% efficiency, 75% efficiency, 80% efficiency, 90% efficiency, 95% efficiency, or 99% or more efficiency) as compared to that of a control, e.g., a corresponding (e.g., analogous) tRNA/RS endogenous pair, or an active orthogonal pair (e.g., a tryptophanyl orthogonal tRNA/RS pair). "Improvement in orthogonality" refers to enhanced orthogonality (e.g., improved efficiency of orthogonal pairs and/or reduced efficiency of orthogonal components in pairs with endogenous translation components) compared to given starting components.

The term "analogous", as used herein, refers to components that provide similar functions but originate from different systems. For example, a *Bacillus* tRNA$^{Trp}$ and a *Saccharomyces* tRNA$^{Trp}$ perform similar functions but originate in different translation systems. As used herein, derivative (e.g., artificial) components of biological systems can be considered analogous to natural components.

The term "derivative", as used herein, refers to chemical (e.g., biological) compounds that are derived from a parent compound, e.g., by a chemical reaction with, or mutagenesis of, the parent compound, or by synthesis of the parent compound in a modified form (thereby forming a chemical analog of the parent compound). A derivative can be a compound derived from a chemical modification of a parent compound, such as, e.g., addition or removal of a chemical group, changing the molecular bond structure, or changing an ionic state. A derivative nucleic acid or peptide can have a naturally polymerized sequence (e.g., produced by mutation) and/or a synthetic sequence modified from that of a purified or known parent sequence. Derivative nucleic acids or polypeptides of the invention can include, e.g., functional conservative variations of sequences described herein.

The term "translation system" refers to the components necessary to incorporate an amino acid into a growing polypeptide chain (e.g., protein). For example, a translation system can include a full set of endogenous translation components, such as ribosomes, tRNAs, synthetases, mRNA, and the like. The orthogonal components of the present invention (e.g., O-tRNAs, O-RSs, nucleic acids encoding selector codons, and/or unnatural amino acids) can be added to an in vitro or in vivo translation system having endogenous components, e.g., a non-eukaryotic cell, e.g., a bacterium (such as *E. coli*), or a eukaryotic cell, e.g., a yeast cell, a mammalian cell, a plant cell, an algae cell, a fungus cell, an insect cell, and/or the like.

As used herein, the term "eukaryote" refers to organisms belonging to the phylogenetic domain Eucarya, such as animals (e.g., mammals, insects, reptiles, birds, etc.), ciliates, plants (e.g., monocots, dicots, algae, etc.), fungi, yeasts, flagellates, microsporidia, protists, etc.

As used herein, the term "non-eukaryote" refers to non-eukaryotic organisms. For example, a non-eukaryotic organism can belong to the Eubacteria (e.g., *Escherichia coli, Thermos thermophilus, Bacillus stearothermophilus*, etc.) phylogenetic domain, or the Archaea (e.g., *Methanococcus jannaschii* (Mj), *Methanosarcina mazei* (Mm), *Methanobac-* terium thermoautotrophicum (Mt), Methanococcus maripaludis, Methanopyrus kandleri, Halobacterium such as Haloferax volcanii and Halobacterium species NRC-1, Archaeoglobus fulgidus (Af), Pyrococcus fitriosus (Pf), Pyrococcus horikoshii (Ph), Pyrobaculum aerophilum, Pyrococcus abyssi, Sulfolobus solfataricus (Ss), Sulfolobus tokodaii, Aeuropyrum pernix (Ap), Thermoplasma acidophilum, Thermoplasma volcanium, etc.) phylogenetic domains.

The term "complementary" with reference to components of a translation system refers to components that can function together. An orthogonal O-tRNA/O-RS pair, e.g., that functions to effectively aminoacylate the O-tRNA can be considered a complimentary pair.

A "suppressor tRNA" is a tRNA that alters the reading of a messenger RNA (mRNA) in a given translation system, e.g., by providing a mechanism for incorporating an amino acid into a polypeptide chain in response to a selector codon. For example, a suppressor tRNA can read through, e.g., a stop codon, a four base codon, a rare codon, etc.

As used herein, the term "suppression activity" refers, in general, to the ability of a tRNA (e.g., a suppressor tRNA) to allow translational read-through of a codon (e.g. a selector codon that is an amber codon or a 4-or-more base codon) that would otherwise result in the termination of translation or mistranslation (e.g., frame-shifting). Suppression activity of a suppressor tRNA can be expressed as a percentage of translational read-through activity observed compared to a second suppressor tRNA, or as compared to a control system, e.g., a control system lacking an O-RS.

As used herein, the term "encode" refers to any process whereby the information in a polymeric macromolecule or sequence string is used to direct the production of a second molecule or sequence string that is different from the first molecule or sequence string. As used herein, the term is used broadly, and can have a variety of applications. In one aspect, the term "encode" describes the process of semi-conservative DNA replication, where one strand of a double-stranded DNA molecule is used as a template to encode a newly synthesized complementary sister strand by a DNA-dependent DNA polymerase.

In another aspect, the term "encode" refers to any process whereby the information in one molecule is used to direct the production of a second molecule that has a different chemical nature from the first molecule. For example, a DNA molecule can encode an RNA molecule (e.g., by the process of transcription incorporating a DNA-dependent RNA polymerase enzyme). Also, an RNA molecule can encode a polypeptide, as in the process of translation. When used to describe the process of translation, the term "encode" also extends to the triplet codon that encodes an amino acid. In some aspects, an RNA molecule can encode a DNA molecule, e.g., by the process of reverse transcription incorporating an RNA-dependent DNA polymerase. In another aspect, a DNA molecule can encode a polypeptide, where it is understood that "encode" as used in that case incorporates both the processes of transcription and translation.

The term "cognate" refers to components that function together, e.g., an orthogonal tRNA and an orthogonal aminoacyl-tRNA synthetase that preferentially aminoacylates the cognate orthogonal tRNA; or a cognate unnatural amino acid that is effectively incorporated into a peptide by an orthogonal RS/tRNA pair. The functionally paired components can also be referred to as being "complementary."

As used herein, proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. For example, any naturally occurring nucleic acid can be modified by any available mutagenesis method to include one or more selector codon. When expressed, this mutagenized nucleic acid can encode a polypeptide comprising one or more unnatural amino acid. The mutation process can, of course, additionally alter one or more standard codon, thereby changing one or more standard amino acid in the resulting mutant protein as well. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95%, or 99%, or more, can also be used to establish homology. Methods for determining sequence similarity percentages (e.g., BLASTP and BLASTN using default parameters) are described herein and are generally available.

As used herein, the term "derived from" refers to a component that is isolated from or made using a specified molecule or organism, or sequence information from the specified molecule or organism.

The term "conservative variant" refers to a translation component, e.g., a conservative variant O-tRNA or a conservative variant O-RS, that functionally performs like the component from which the conservative variant is based, e.g., an O-tRNA or O-RS, but having variations in the sequence. For example, an O-RS will aminoacylate a complementary O-tRNA or a conservative variant O-tRNA with an unnatural amino acid, e.g., a 5-HTPP, although the O-tRNA and the conservative variant O-tRNA do not have the same sequence. The conservative variant can have, e.g., one variation, two variations, three variations, four variations, or five or more variations in sequence, as long as the conservative variant functions when paired (remains complimentary) with to the corresponding O-tRNA or O-RS. See Table 1 for typical conservative variations in amino acid sequences.

The term "unnatural amino acid", as used herein, refers to an amino acid that is not a member of the 20 natural amino acids normally incorporated into proteins in most living systems, or the rare natural amino acids seleno cysteine or pyrrolysine. An "unnatural amino acid" refers to any amino acid, modified amino acid, or amino acid analogue other than the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. The generic structure of an alpha-amino acid is illustrated by Formula I:

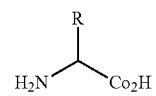

An unnatural amino acid is typically any structure having Formula I wherein the R group is any substituent side chain group) other than one used in the twenty natural amino acids. See, e.g., any biochemistry text such as *Biochemistry* by L. Stryer, $3^{rd}$ ed. 1988, Freeman and Company, New York, for structures of the twenty natural amino acids. Note that, the unnatural amino acids of the present invention may be naturally occurring compounds other than the twenty alpha-amino acids above. Because the unnatural amino acids of the invention typically differ from the natural amino acids in side chain only, the unnatural amino acids form amide bonds with other amino acids, e.g., natural or unnatural, in the same manner in which they are formed in naturally occurring proteins. However, the unnatural amino acids can have side chain groups that distinguish them from the natural amino acids. For example, R in Formula I optionally comprises an unusual alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like, or any combination thereof. Other unnatural amino acids of interest include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto containing amino acids, amino acids comprising polyethylene glycol or polyether, heavy atom substituted amino acids, chemically cleavable and/or photocleavable amino acids, amino acids with an elongated side chains as compared to natural amino acids, e.g., polyethers or long chain hydrocarbons, e.g., greater than about 5 or greater than about 10 carbons, carbon-linked sugar-containing amino acids, redox-active amino acids, amino thioacid containing amino acids, and amino acids comprising one or more toxic moiety. Exemplary, preferred unnatural amino acids of the invention include, e.g., tryptophan derivatives, such as 5-hydroxy-L-tryptophan (5-HTPP).

The term "a construct", as used herein, refers to a nucleic acid construct including synthetic and/or recombinant sequences of interest. Constructs of the invention can include, e.g., nucleic acid sequences encoding orthogonal aminoacyl-tRNA synthetases, orthogonal tRNAs, and/or peptide encoding sequences with selector codons. Constructs can include other sequences, such as, e.g., transcription and translation terminators, transcription and translation initiation sequences, flanking sequences, and/or promoters useful for regulation of expression, etc. Constructs can include sequences encoding tags and/or labels useful in identification and purification of transcription products. Constructs of the invention can be, e.g., in the form of plasmids with sequences transcribable and/or translatable in vivo and/or in vitro.

The term "introducing", as used herein with reference constructs of the invention, generally refers to any means known in the art to functionally insert genetic constructs of the invention into a living cell for replication, transcription, translation, and/or expression. For example, introducing constructs into a cell include transformation, transduction, transfection, electroporation, and/or the like.

BRIEF DESCRIPTION OF THE DRAWINGS

FIG. 2 shows expression and Northern blot analysis of mutRNA$_{UCA}^{Trp}$ obtained from 293T cells transfected with pTrptRNA.

FIG. 7 shows a schematic diagram of electrochemical protein cross-linking. FIG. 7A1 shows a dimerization product of oxidized 5-HTPP molecules; FIG. 7A2 shown a reaction product for oxidized 5-HTPP and cysteine.

DETAILED DESCRIPTION

Figure 1:
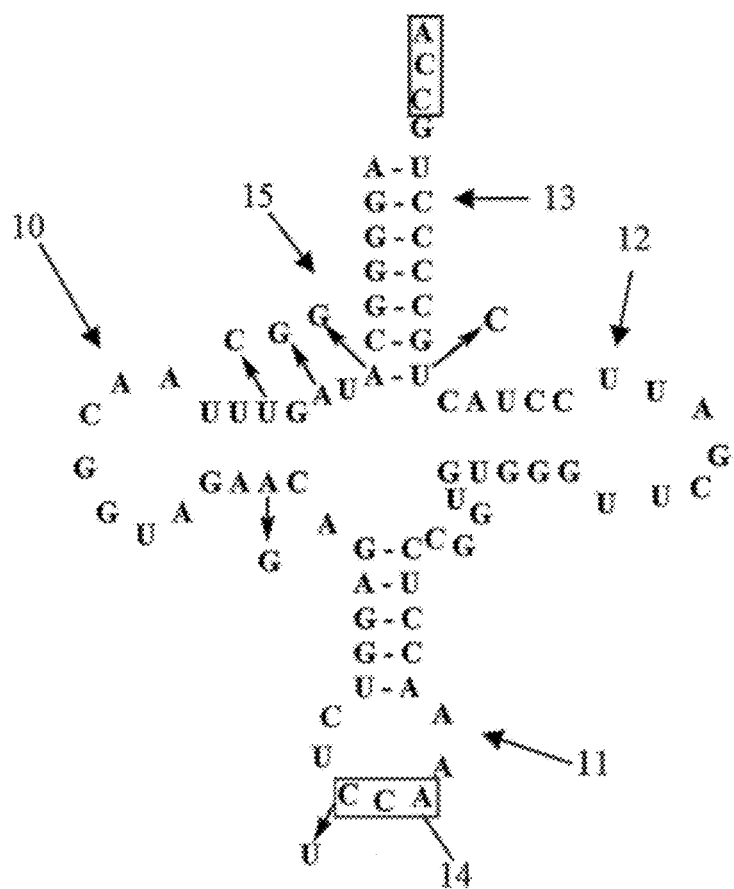
FIG. 1 is a schematic diagram showing the cloverleaf structure of the B. subtilis tryptophan opal suppressor tRNA (SEQ ID NO: 4). The arrows indicate mutations engineered into the sequence. The upper box indicates the CCA sequence deleted from the acceptor arm in the mutRNA$_{UCA}^{Trp}$ (SEQ ID NO. 3) of the invention.

In order to incorporate unnatural amino acids, such as a 5-hydroxy-L-tryptophan (5-HTPP), into a peptide in the translation process, efficiently functioning orthogonal pairs of an aminoacyl-tRNA synthetase and a tRNA can be employed as described herein. An orthogonal pair can function, e.g., in a translation system of interest, independent from the synthetases and tRNAs endogenous to the translation system. Desired characteristics of the orthogonal pair include, e.g., a tRNA that decodes or recognizes only a specific new codon (e.g., a selector codon) that is not decoded efficiently by any endogenous tRNA, and an aminoacyl-tRNA synthetase that preferentially aminoacylates (or charges) its tRNA only with a specific non-natural amino acid, such as 5-HTPP. The orthogonal tRNA (O-tRNA) is also desirably not significantly aminoacylated by endogenous synthetases of the translation system. For example, in an *E. coli* translation system, an orthogonal pair can include an aminoacyl-tRNA synthetase that does not substantially aminoacylate any of the endogenous tRNAs, e.g., of which there are 40 in *E. coli*, and an orthogonal tRNA that is not aminoacylated by any of the endogenous synthetases, e.g., of which there are 21 in *E. coli*.

Here we report the generation of new orthogonal synthetase/tRNA pairs that include orthogonal tryptophanyl-tRNA synthetases, mutant orthogonal tryptophanyl-tRNA synthetases (O-muTrpRS), and/or derivatives thereof, e.g., capable of incorporating amino acids or unnatural amino acids (e.g., tryptophan derivatives) into peptides. The present invention includes methods of, e.g., introducing nucleic acid construct preparations into cells wherein an O-tRNA is preferentially aminoacylated with an amino acid by an O-muTrpRS for incorporation of the amino acid into a peptide.

In a typical embodiment, an orthogonal pair of a mutant tRNA opal suppressor and mutant tryptophanyl-tRNA synthetase (O-tRNA/O-RS pair) is logically constructed and screened for the ability to specifically charge and incorporate 5-hydroxytryptophan (5-HTPP) into a peptide during translation in a mammalian system. The O-tRNA can be provided, e.g., by constructing a mutant *Bacillus subtilis* tRNA$^{Trp}$ with an opal mutation anticodon loop. The O-RS can be provided, e.g., by screening mutant *Bacillus subtilis* tryptophanyl-tRNA synthetases having site directed mutations providing 19 alternate amino acids at a position identified as probably causing steric hindrance to a tRNA charged with 5-HTPP. The O-tRNA/O-RS pair in a mammalian cell in the presence of media containing 5-HTPP can specifically incorporate 5-HTPP into a protein at a position encoded by a TGA (termination) codon.

Compositions Having Orthogonal Translation Components

Compositions, of the invention typically include, e.g., a translation system having an orthogonal tRNA (O-tRNA) and an orthogonal tryptophanyl-tRNA synthetase (O-TrpRS) to preferentially charge the O-tRNA with an amino acid for incorporation into a peptide at a position designated by a selector codon. Optionally, the synthetase can be a mutant orthogonal tryptophanyl-tRNA synthetase specifically engineered and/or selected to charge the O-tRNA with a particular unnatural amino acid, such as, e.g., 5-HTPP.

Orthogonal translation system components of the invention are generally, e.g., analogs of endogenous components, such as mutated components and/or components from foreign cells, that can accomplish some translation functions independent from the endogenous translation system of interest. Orthogonal translation components often operate with reduced efficiency, or have an inability to function, with some endogenous translation system components. However, complimentary orthogonal components, such as an O-RS/O-tRNA pair (orthogonal pair) can function efficiently along with components of an endogenous translation system to successfully participate in translation of a sequence. For example, an orthogonal pair can work as part of a translation system to efficiently incorporate specific amino acids into positions of a growing peptide governed by a specific selector codon.

The invention features multiple O-tRNA/O-RS pairs in a cell or other translation system, allowing incorporation of more than one unnatural amino acid, e.g., a 5-HTPP and another unnatural amino acid. For example, the cell can include an orthogonal pair of the invention and an additional different O-tRNA/O-RS pair and a second unnatural amino acid, where this additional O-tRNA recognizes a second selector codon and this additional O-RS preferentially aminoacylates the O-tRNA with the second unnatural amino acid. For example, a cell that includes an O-tRNA/O-RS pair (where the O-tRNA recognizes, e.g., an opal selector codon), can further comprise a second orthogonal pair, e.g., leucyl, lysyl, glutamyl, etc., (where the second O-tRNA recognizes a different selector codon, e.g., an amber, four-base codon, rare codons or the like).

Orthogonal Tryptophanyl-tRNA Synthetases

Orthogonal aminoacyl-tRNA synthetases (O-RSs) of the invention can include, e.g., orthogonal tryptophanyl-tRNA synthetases (O-TrpRSs, e.g., substantially unmodified RSs from a foreign translation system), orthogonal mutant tryptophanyl-tRNA synthetases (O-muTrpRSs, e.g., endogenous or foreign RSs modified, e.g., by mutation), and/or derivatives thereof. O-RSs of the invention can, e.g., charge a tRNA with an amino acid for incorporation of the amino acid into a peptide at a position not normally available for that amino acid through the endogenous translation system. In a typical embodiment, the O-RS is an O-muTrpRS that charges a tRNA with an unnatural amino acid, such as 5-HTPP. The unnatural amino acid can then be incorporated by a translation system into a growing peptide chain at a position determined by the anticodon of the tRNA. In another embodiment, an O-TrpRS or O-muTrpRS can charge an orthogonal tRNA (O-tRNA) with an amino acid. The O-tRNA can have an anticodon complimentary to, e.g., a selector codon, or other codon not normally coding for the amino acid, so that the amino acid is incorporated into a growing peptide at a position not typical of a normal translation. In a preferred embodiment, the O-RS of the invention preferentially aminoacylates an O-tRNA with an unnatural amino acid. In a more preferred embodiment, the unnatural amino acid is an analog (e.g., derivative) of tryptophan.

Orthogonal aminoacyl-tRNA synthetases of the invention can demonstrate preferential aminoacylation, e.g., of an O-tRNA with an unnatural amino acid. O-TrpRSs or O-muTrpRSs of the invention can charge a tRNA preferentially with one amino acid over another. For example, an O-muTrpRS constructed as a mutant form of a natural RS that charges a tRNA with a cognate amino acid can preferentially charge the tRNA with a different amino acid over the original cognate amino acid. O-RSs of the invention can preferentially charge a tRNA with the different amino acid over an original cognate amino acid in a proportion greater than 1 to 1, about 2 to 1, about 4 to 1, about 5 to 1, about 20 to 1, about 100 to 1, or more. The O-RSs of the invention can preferentially aminoacylate (charge) an O-tRNA with a natural or unnatural amino acid over charging an endogenous (e.g., analogous) tRNA. For example, if the O-tRNA is a mutated form of an endogenous tRNA, the O-RS of the invention can preferentially charge the O-tRNA over the tRNA in a proportion greater than 1 to 1, about 2 to 1, about 4 to 1, about 5 to 1, about 20 to 1, about 100 to 1, or more.

The activity of O-RSs of the invention can be adequate to provide useful amounts of transcription product. In a preferred embodiment, the O-RS is active in charging its cognate amino acid to its paired (complimentary) O-tRNA at rates representing a substantial proportion of a typical rate for endogenous RS/tRNA pairs in the translation system. For example, an orthogonal pair (O-RS/O-tRNA) of the invention can charge the O-tRNA with its cognate (optionally unnatural, e.g., 5-HTPP) amino acid at with an activity about 1%, about 5%, about 10%, about 25%, about 50%, about 80%, about 90%, about 100%, or more, of an endogenous (optionally analogous) RS in a translation system. In another aspect, an O-RS of the invention in a translation system of interest can aminoacylate any endogenous tRNA with reduced or even zero efficiency, when compared to aminoacylation of an endogenous tRNA by a cognate endogenous RS. In many cases, O-RSs of the invention are capable of aminoacylating a cognate tRNA with an unnatural amino acid, yet are relatively ineffective at aminoacylating the tRNA with a natural amino acid. Such an O-RS of the invention can have improved or enhanced enzymatic properties, e.g., the $K_m$ is lower, the $k_{cat}$ is higher, the value of $k_{cat}/K_m$ is higher or the like, for the unnatural amino acid compared to a naturally occurring amino acid, e.g., one of the 20 known amino acids. This can be considered preferred aminoacylation of the tRNA by the O-RS. Values of $k_{cat}$ and $K_m$ can be calculated, e.g., by direct fitting of the Michaelis-Menton equation using nonlinear regression analysis, as is well known in the art.

O-RSs and orthogonal pairs of the invention can provide faithful incorporation of their cognate (optionally unnatural, e.g., 5-HTPP) amino acid into a growing peptide. O-RSs and orthogonal pairs can correctly incorporate their cognate amino acid into a growing peptide with high fidelity. For example, the cognate amino acid, such as 5-HTPP, can be incorporated at the position determined by the anticodon of the associated tRNA (e.g., O-tRNA) in a peptide chain with a fidelity of greater than 70%, about 90%, about 95%, about 97%, about 99%, or substantially 100% fidelity. O-RSs and orthogonal pairs of the invention can provide faithful incorporation of: natural or unnatural amino acids into positions corresponding to codons of other amino acids, or incorporation natural or unnatural amino acids into positions corresponding to selector codons (such as, termination codons or four base codons).

In a preferred embodiment, the O-RS of the invention is a mutant tryptophanyl-tRNA synthetase (O-muTrpRS). The O-muTrpRS can be, for example: a modified version of a tryptophanyl-tRNA synthetase (TrpRS) endogenous to a translation system of interest, a modified (e.g., mutated) TrpRS from a foreign (e.g., different kingdom, family, genus, or species) translation system, a TrpRS mutated and screened for activity with a natural or unnatural amino acid of interest, a TrpRS mutated and screened for activity with a tRNA or O-tRNA of interest, a TrpRS mutated (e.g., by site-directed mutation) at a position identified based on structural (e.g., crystallography) data, and/or derivatives thereof. In a more preferred embodiment, the O-muTrpRS can be a foreign TrpRS mutated to preferentially aminoacylate a tRNA with a tryptophan analog. In a more preferred embodiment, O-muTrpRS can be a *Bacillus* TrpRS mutated at a codon for valine in a region near about residue 144. In a more preferred embodiment, the O-muTrpRS has the amino acid sequence of SEQ ID NO: 2 (the Val144ProBsTrpRS amino acid sequence), or a conservative substitution thereof. In a more preferred embodiment, the O-muTrpRS has the amino acid sequence encoded by the nucleic acid sequence of SEQ ID NO: 1 (the nucleic acid sequence encoding Val144ProBsTrpRS), or conservative variations thereof. For example, the first two bases of the codon for valine residue 144 can be mutated from "GT" to "CC" to encode proline at residue 144. In a most preferred embodiment, the O-muTrpRS can be a *Bacillus subtilis* TrpRS mutated Val144Pro for use incorporating 5-hydroxy-L-tryptophan in a mammalian translation system.

Orthogonal tRNAs

Orthogonal tRNAs (O-tRNA) of the invention can be charged, e.g., with a reduced efficiency by endogenous aminoacyl-tRNA synthetases of a translation system, yet can be effectively charged with a natural or unnatural amino acid by a cognate O-RS of the invention. In a typical embodiment, the O-tRNA is charged by an O-RS with an unnatural amino acid. The unnatural amino acid aminoacylated onto the O-tRNA can be incorporated by the translation system into a growing peptide chain at a position determined by the anticodon of the O-tRNA. In another embodiment, the O-tRNA of the invention can be charged by an endogenous RS with a natural or unnatural amino acid, e.g., to offer the amino acid for incorporation at an unusual position in a growing peptide chain, according to the anticodon of the O-tRNA. In a preferred embodiment, the O-tRNA of the invention is preferentially aminoacylated by an O-RS of the invention with an unnatural amino acid, such as, e.g., 5-HTPP.

Transfer ribonucleic acids (tRNAs) generally have D arm 10, anticodon loop 11, C arm 12, and acceptor arm 13, as shown in FIG. 1. The sequence of A, U, G, and C bases (adenosine, uracil, guanine, and cytosine, respectively) in tRNAs can vary depending on its cognate amino acid, the type of cell it is found in, mutations, genetic manipulations, and the like. An important part of a tRNA sequence is the anticodon loop and associated anticodon 14 that bind to complimentary codons on messenger RNA (mRNA) during transcription to present the appropriate amino acid to a growing peptide chain. As there are 4 bases, and 3 bases per codon, there are 64 possible triplet codons to designate the 20 natural amino acids. Of the 64 triplet codons, three (UUA, CUA, and UCA in mRNA; corresponding transcripts from TAA, TAG, and TGA in DNA) designate termination of translation and are not normally used to code for an amino acid. Suppressor tRNAs with anticodons complimentary to the termination codons to provide an amino acid at stop positions are known to occur naturally. In one aspect of the invention, O-tRNAs can include an anticodon complimentary to a termination codon and thus insert an amino acid into a growing peptide chain at a position corresponding to a stop codon.

The invention includes conservative variations of O-tRNAs corresponding to particular O-tRNAs herein. For example, conservative variations of O-tRNA include those molecules that function like the O-tRNAs of the sequence listing SEQ ID NO: 3 and that maintain the tRNA L-shaped structure by virtue of appropriate self-complementarity, but that do not have a sequence identical to those, e.g., in the sequence listing, figures, or examples herein (and, desirably, are other than wild type tRNA molecules). See also, the section below entitled "Conservative Variations." An O-tRNA of the invention can include, e.g., an artificial polynucleotide that is, e.g., at least 75%, at least 80%, at least 90%, at least 95%, at least 98% or more identical to that of a naturally occurring tRNA, (but is other than a naturally occurring tRNA) or any tRNA in a listing or example herein.

O-tRNAs of the invention can optionally include a variety of other anticodons. An O-tRNA can have an anticodon normally reserved for one amino acid yet be charged with another amino acid. An O-tRNA can have an anticodon complimentary to a codon of more than 3 bases, such as a 4 base or 5 base codon. An O-tRNA can have an anticodon that contains unnatural bases or which is complimentary to a codon containing unnatural bases. Selector codons can be extended codons, e.g., four or more base codons, such as, four, five, six or more base codons. Examples of four base codons include, e.g., AGGA, CUAG, UAGA, CCCU, and the like. Examples of five base codons include, e.g., AGGAC, CCCCU, CCCUC, CUAGA, CUACU, UAGGC and the like. Methods of the invention include using extended codons based on frameshift suppression. Four or more base codons can insert, e.g., one or multiple unnatural amino acids such as a 5-HTPP, into the same protein. In other embodiments, the anticodon loops can decode, e.g., at least a four-base codon, at least a five-base codon, or at least a six-base codon, or more. Since there are 256 possible four-base codons, multiple unnatural amino acids can be encoded in the same cell using a four or more base codon. See Anderson et al., (2002) *Exploring the Limits of Codon and Anticodon Size, Chemistry and Biology*, 9:237-244; and, Magliery, (2001) *Expanding the Genetic Code: Selection of Efficient Suppressors of Four-base Codons and Identification of "Shifty" Four-base Codons with a Library Approach in Escherichia coli, J. Mol. Biol.* 307: 755-769.

Selector codons optionally include unnatural base pairs. These unnatural base pairs can further expand the existing genetic alphabet. For example, provision of one extra functional base pair increases the number of triplet codons from 64 to 125. Desirable properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions of the invention include, e.g., Hirao, et al., (2002) *An unnatural base pair for incorporating amino acid analogues into protein, Nature Biotechnology*, 20:177-182. See also Wu, Y., et al., (2002) *J. Am. Chem. Soc.* 124:14626-14630. For in vivo usage, the unnatural nucleoside is typically membrane permeable and is phosphorylated to form the corresponding triphosphate.

In a preferred embodiment, the O-tRNA of the invention is a mutant suppressor tRNA having a UCA, UUA, or CUA anticodon, complimenting UGA, UAA, and UAG mRNA codons, respectively. In a more preferred embodiment, the O-tRNA is an orthogonal tryptophan charged tRNA (O-tRNA$^{Trp}$), or an orthogonal mutant tRNA (O-mu tRNA$^{Trp}$) that can be specifically charged, e.g., with a natural amino acid (e.g., tryptophan) or an unnatural amino acid (e.g., 5-HTPP). In a more preferred embodiment, the O-tRNA is an orthogonal suppressor mutant tRNA, such as, e.g., an orthogonal mutant opal suppressor tRNA that can be charged with an unnatural amino acid (e.g., mu tRNA$_{UCA}^{Trp}$) with an anticodon complimentary to a UGA termination selector codon.

Typical O-tRNAs of the invention are preferentially aminoacylated by an O-RS as a member of a functional complimentary orthogonal pair. As a member of the orthogonal pair, for example, the O-tRNA is not substantially aminoacylated by endogenous RSs in a translation system of interest, the O-tRNA is preferentially charged with a cognate natural or unnatural amino acid of interest, and is preferentially charged by the cognate O-RS pair member which does not substantially charge other tRNAs with the cognate amino acid. For example, an orthogonal tRNA can be less than 20% as efficient, less than 10% as efficient, less than 5% as efficient, or e.g., less than 1% as efficient, in an aminoacylation reaction with an endogenous RS than when paired with the complimentary O-RS.

In one aspect of the invention, the orthogonal pair can be O-tRNA and O-RS mutants derived from prokaryotic translation systems for addition to a eukaryotic translation system where the O-tRNA is preferentially aminoacylated with an unnatural amino acid by the O-RS for incorporation into a growing peptide chain. In a preferred embodiment, the O-tRNA is derived from a *Bacillus* translation system and paired with a mutant O-RS from a *Bacillus* translation system. In a more preferred embodiment, the O-tRNA is a mutant tRNA$^{Trp}$ from a *Bacillus* translation system and the O-RS is a *Bacillus* RS mutated to preferentially charge the O-tRNA with an unnatural amino acid, such as, e.g., 5-HTPP.

Unnatural Amino Acids Incorporated into Product Peptides

Compositions of the invention can be used in methods of the invention to incorporate natural and/or unnatural amino acids into growing peptide chains. Unnatural amino acids of the invention can be, e.g., any amino acids not a member of the group of 20 natural amino acids well known in the art. The unnatural amino acids can be incorporated into a variety of therapeutic, diagnostic, and industrial proteins to provide beneficial properties.

Unnatural amino acids of the invention can include natural compounds, synthetic compounds, and/or modified natural compounds. For example, naturally occurring amino acids, other than the twenty common alpha-amino acids, or seleno cysteine and pyrrolysine, can be considered unnatural amino acids of the present invention. The unnatural amino acids of the invention typically differ from the natural amino acid due to modifications of side chain groups. The unnatural amino acids typically form amide bonds with other amino acids, e.g., natural or unnatural, in the same manner as they are formed in naturally occurring proteins. In a preferred embodiment, a chemically active group on a natural amino acid is reacted with a reactive molecule to link an additional chemical group to the natural amino acid side chain to produce an unnatural amino acid. In one aspect of the invention, unnatural amino acids are natural amino acids modified by the addition of a chemical group such as, e.g., an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, an amino group, and/or the like.

In another aspect, unnatural amino acids of the invention can be incorporated into a protein to provide new qualities. Unnatural amino acids can provide, e.g., new chemistries, changed antigenicity, a cross linking site, changed light absorbance, changed fluorescence, reporter groups, and/or the like. For example, chemical groups can be added to fluorescent amino acids to change their excitation profile, emission profile, and/or intensity of emissions. For example, the addition of a hydroxy group to tryptophan to form 5-hydroxy-L-tryptophan (5-HTPP) can provide a significant shift in emissions maxima useful in protein probes incorporating 5-HTPP. Chemical groups, such as fluorescent chemical groups, can be added to substantially non-fluorescent amino acids to provide a fluorescent signal from the modified unnatural amino acid. Reactive groups can be added to natural amino acids to form unnatural amino acids with side chains providing, e.g., linkage sites for linkage reactions with commonly available linkers, such as hydroxysuccinimide linkers (reactive with primary amines), maleimide linkers, haloacetyls, pyridyl disulfides (reactive with sulfhydral groups), hydrazine linkers (reactive with aldehydes), and/or ethyldiethylamino propylcarbodiimide (EDC, reactive with carboxyl groups). In an aspect of the invention, the unnatural amino acid can be a redox controllable linker, e.g., reactive in a particular range of voltage potentials and pHs. For example, proteins with incorporated 5-HTPP can react with other reactive molecules in solution at about pH 7.4 with an 800 mV electrical potential. In a preferred embodiment, the other reactive molecule is another protein having an incorporated 5-HTPP and the reaction results in a cross-linking between the proteins, e.g., a dimerization.

Product peptides (e.g., alloproteins) of the invention are typically derivatives of therapeutic proteins, diagnostic proteins, and/or industrial enzymes, of interest. The product peptides are, e.g., at least 60%, at least 70%, at least 75%, at least 80%, at least 90%, at least 95%, or at least 99% or more identical to the proteins of interest, and they comprise one or more unnatural amino acid. Examples of therapeutic, diagnostic, industrial, and other proteins that can be modified to comprise one or more 5-HTPP can be found, but not limited to, those in U.S. Ser. Nos. 60/479,931, and 60/496,548 entitled "Expanding the Eukaryotic Genetic Code;" and, WO 2002/085923, entitled "In Vivo Incorporation of Unnatural Amino Acids." Examples of therapeutic, diagnostic, and other proteins that can be modified to comprise one or more 5-HTPP residues include, but are not limited to, e.g., alpha-1 antitrypsin, angiostatin, antihemolytic factor, antibodies, apolipoprotein, apoprotein, atrial natriuretic factor, atrial natriuretic polypeptide, atrial peptides, C—X—C chemokines (e.g., T39765, NAP-2, ENA-78, Gro-a, Gro-b, Gro-c, IP-10, GCP-2, NAP-4, SDF-1, PF4, MIG), calcitonin, CC chemokines (e.g., monocyte chemoattractant protein-1, monocyte chemoattractant protein-2, monocyte chemoattractant protein-3, monocyte inflammatory protein-1 alpha, monocyte inflammatory protein-1 beta, RANTES, I309, R83915, R91733, HCC1, T58847, D31065, T64262), CD40 ligand, C-kit Ligand, collagen, colony stimulating factor (CSF), complement factor 5a, complement inhibitor, complement receptor 1, cytokines, (e.g., epithelial neutrophil activating peptide-78, GROα/MGSA, GROβ, GROγ, MIP-1α, MIP-1δ, MCP-1), epidermal growth factor (EGF), erythropoietin ("EPO"), exfoliating toxins A and B, Factor IX, Factor VII, Factor VIII, Factor X, fibroblast growth factor (FGF), fibrinogen, fibronectin, G-CSF, GM-CSF, glucocerebrosidase, gonadotropin, growth factors, hedgehog proteins (e.g., Sonic, Indian, Desert), hemoglobin, hepatocyte growth factor (HGF), hirudin, human serum albumin, insulin, insulin-like growth factor (IGF), interferons (e.g., IFN-α, IFN-β, IFN-γ), interleukins (e.g., IL-1, IL-2, IL-3, IL-4, IL-5, IL-6, IL-7, IL-8, IL-9, IL-10, IL-12, etc.), keratinocyte growth factor (KGF), lactoferrin, leukemia inhibitory factor, luciferase, neurturin, neutrophil inhibitory factor (NIF), oncostatin M, osteogenic protein, parathyroid hormone, PD-ECSF, PDGF, peptide hormones (e.g., human growth hormone), pleiotropin, protein A, protein G, pyrogenic exotoxins A, B, and C, relaxin, renin, SCF, soluble complement receptor I, soluble I-CAM 1, soluble interleukin receptors (IL-1, 2, 3, 4, 5, 6, 7, 9, 10, 11, 12, 13, 14, 15), soluble TNF receptor, somatomedin, somatostatin, somatotropin, streptokinase, superantigens, i.e., staphylococcal enterotoxins (SEA, SEB, SEC1, SEC2, SEC3, SED, SEE), superoxide dismutase (SOD), toxic shock syndrome toxin (TSST-1), thymosin alpha 1, tissue plasminogen activator, tumor necrosis factor beta (TNF beta), tumor necrosis factor receptor (TNFR), tumor necrosis factor-alpha (TNF alpha), vascular endothelial growth factor (VEGEF), urokinase, and many others.

One class of proteins that can be made using the compositions and methods for in vivo incorporation of 5-HTPP residues includes transcriptional modulators or portions thereof. Exemplary transcriptional modulators include genes and transcriptional modulator proteins that modulate cell growth, differentiation, regulation, or the like. Transcriptional modulators are found in prokaryotes, viruses, and eukaryotes, including fungi, plants, yeasts, insects, and animals, including mammals, providing a wide range of therapeutic targets. It will be appreciated that expression and transcriptional activators regulate transcription by many mechanisms, e.g., by binding to receptors, stimulating a signal transduction cascade, regulating expression of transcription factors, binding to promoters and enhancers, binding to proteins that bind to promoters and enhancers, unwinding DNA, splicing pre-mRNA, polyadenylating RNA, and degrading RNA.

One class of product peptides of the invention (e.g., proteins that can be usefully modified by incorporation of one or more unnatural amino acids, such as 5-HTPP or other tryptophan derivative residue) include expression activators such as cytokines, inflammatory molecules, growth factors, their receptors, and oncogene products, e.g., interleukins (e.g., IL-2, IL-8, etc.), interferons, FGF, IGF-I, FGF, PDGF, TNF, TGF-α, TGF-β, EGF, KGF, SCF/c-Kit, CD40L/CD40, VLA-4/VCAM-1, ICAM-1/LFA-1, and hyalurin/CD44; signal transduction molecules and corresponding oncogene products, e.g., Mos, Ras, Raf, and Met; and transcriptional activators and suppressors, e.g., p53, Tat, Fos, Myc, Jun, Myb, Rel, and steroid hormone receptors such as those for estrogen, progesterone, testosterone, aldosterone, the LDL receptor ligand, and corticosterone.

Enzymes (e.g., industrial enzymes or medicinal enzymes) or portions thereof with at least one 5-HTPP or other tryptophan derivative residue are also provided by the invention. Examples of enzymes include, but are not limited to, e.g., amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases.

Many of these proteins are commercially available (See, e.g., the Sigma BioSciences 2003 catalogue and price list), and the corresponding protein sequences and genes and, typically, many variants thereof, are well-known (see, e.g., Genbank). Any of them can be modified by the insertion of, e.g., one or more unusual amino acid or tryptophan derivative according to the invention, e.g., to alter the protein with respect to one or more therapeutic, diagnostic or enzymatic properties of interest. Examples of therapeutically relevant properties include modified pharmacokinetics, serum half-life, shelf half-life, stability, immunogenicity, therapeutic activity, detectability (e.g., by the inclusion of reporter groups (e.g., labels or label binding sites) in the unnatural amino acids, e.g., 5-HTPP), reduction of $LD_{50}$ or other side effects, ability to enter the body through the gastric tract (e.g., oral availability), or the like. Examples of diagnostic properties include shelf half-life, stability, diagnostic activity, detectability, or the like. Examples of relevant enzymatic properties include shelf half-life, stability, heat tolerance, enzymatic activity, production capability, or the like.

A variety of other proteins can also be modified to include one or more unnatural amino acid of the invention. For example, the invention can include substituting one or more natural amino acids in one or more vaccine proteins with a 5-HTPP, e.g., in proteins from infectious fungi, e.g., *Aspergillus, Candida* species; bacteria, particularly *E. coli*, which serves a model for pathogenic bacteria, as well as medically important bacteria such as *Staphylococci* (e.g., *aureus*), or *Streptococci* (e.g., *pneumoniae*); protozoa such as sporozoa (e.g., *Plasmodia*), rhizopods (e.g., *Entamoeba*) and flagellates (*Trypanosoma, Leishmania, Trichomonas, Giardia*, etc.); viruses such as (+) RNA viruses (examples include Poxviruses e.g., vaccinia; Picornaviruses, e.g. polio; Togaviruses, e.g., rubella; Flaviviruses, e.g., HCV; and Coronaviruses), (−) RNA viruses (e.g., Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., HIV and HTLV, and certain DNA to RNA viruses such as Hepatitis B.

Agriculturally related proteins such as insect resistance proteins (e.g., the Cry proteins), starch and lipid production enzymes, plant and insect toxins, toxin-resistance proteins, Mycotoxin detoxification proteins, plant growth enzymes (e.g., ribulose 1,5-bisphosphate carboxylase/oxygenase, "RUBISCO"), lipoxygenase (LOX), and phosphoenolpyruvate (PEP) carboxylase are also suitable targets for modification with unnatural amino acids of the invention.

Source and Host Organisms

The orthogonal translational components of the invention are typically derived from non-eukaryotic organisms. For example, the O-tRNA can be derived from a non-eukaryotic organism (or a combination of organisms), e.g., an archaebacterium, such as *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum penxix, Methanococcus maripaludis, Methanopyrus kandleri, Methanosarcina mazei* (Mm), *Pyrobaculum aerophilum, Pyrococcus abyssi, Sulfolobus solfataricus* (Ss), *Sulfolobus tokodaii, Thermoplasma acidophilum, Thermoplasma volcanium*, or the like, or a eubacterium, such as *Escherichia coli, Thermus thermophilus, Bacillus stearothermophilus*, or the like, while the orthogonal O-RS of the invention can be derived from a non-eukaryotic organism (or a combination of organisms), e.g., an archaebacterium, such as *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix, Methanococcus maripaludis, Methanopyrus kandleri, Methanosarcina mazei, Pyrobaculum aerophilum, Pyrococcus abyssi, Sulfolobus solfataricus, Sulfolobus tokodaii, Thermoplasma acidophilum, Thermoplasma volcanium*, or the like, or a eubacterium, such as *Escherichia coli, Thermus thermophilus, Bacillus stearothermphilus*, or the like. In one embodiment, eukaryotic sources, e.g., plants, algae, protists, fungi, yeasts, animals (e.g., mammals, insects, arthropods, etc.), or the like, can also be used as sources of O-tRNAs and/or O-RSs, or sources for construction of mutant O-tRNAs and/or mutant O-RSs.

The individual components of an O-tRNA/O-RS pair of the invention can be derived from the same organism or different organisms. In one embodiment, the O-tRNA/O-RS pair is from the same organism. Alternatively, the O-tRNA and the O-RS of the O-tRNA/O-RS pair can be from different organisms. In one preferred example embodiment, a tryptophanyl synthetase/tRNA pair of *Bacillus subtilis* is used as an orthogonal pair, e.g., in a mammalian cell-based translation system. As described herein, this pair can be modified to recognize an opal mutant selector codon and can be modified to specifically charge the O-tRNA with an unusual or unnatural amino acid, such as 5-HTPP. This orthogonal pair (or modified forms thereof) can also be combined with previously described orthogonal pairs, e.g., those derived from *Methanococcus jannaschii*, e.g., that are modified to recognize stop selector codons. This provides for production of proteins that comprise two different unnatural amino acids in a translation system of interest.

Orthogonal components of the invention can function in in vivo translation systems found in a variety of living cells. The O-tRNA, O-RS, or O-tRNA/O-RS pairs of the invention can be selected or screened in vivo or in vitro and/or used in a cell, e.g., a non-eukaryotic cells, or eukaryotic cells, to produce a polypeptide with a 5-HTPP residue in a translation system. A non-eukaryotic cell can be from a variety of sources, e.g., a eubacterium, such as *Escherichia coli, Thermus thermophilus, Bacillus subtilis, Bacillus stearothermophilus*, or the like, or an archaebacterium, such as *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix, Methanococcus maripaludis, Methanopyrus kandleri, Methanosarcina mazei* (Mm), *Pyrobaculum aerophilum, Pyrococcus abyssi, Sulfolobus solfataricus* (Ss), *Sulfolobus tokodaii, Thermoplasma acidophilum, Thermoplasma volcanium*, or the like. A eukaryotic cell can be from a variety of sources, e.g., a plant (e.g., complex plant such as monocots, or dicots), an algae, a protist, a fungus, a yeast (e.g., *Saccharomyces cerevisiae*), an animal (e.g., a mammal, an insect, an arthropod, etc.), or the like. Compositions of cells with translational components of the invention are also a feature of the invention.

See also, U.S. Ser. Nos. 60/479,931, and 60/496,548 entitled "Expanding the Eukaryotic Genetic Code" for screening O-tRNA and/or O-RS in one species for use in another species.

Nucleic Acid and Polypeptide Sequence Variants

The present invention provides for nucleic acid polynucleotide sequences and polypeptide amino acid sequences, e.g., for O-tRNAs and O-RSs, and, e.g., compositions and methods comprising said sequences. Exemplary sequences for, e.g., O-tRNAs and O-RSs of the invention are disclosed herein. However, one of skill in the art will appreciate that the invention is not limited to only those specific sequences. One of skill will appreciate that the present invention also provides many related and unrelated sequences providing, e.g., functional O-tRNAs, O-muTrpRSs, O-TrpRSs, alloproteins, and the like.

One of skill will also appreciate that many variants of the disclosed sequences are included in the invention. For example, conservative variations of the disclosed sequences that yield a functionally identical sequence are included in the invention. Variants of the nucleic acid polynucleotide sequences, wherein the variants, or complimentary sequence of the variants, hybridize to at least one disclosed sequence, are considered to be included in the invention. Unique subsequences of the sequences disclosed herein, as determined by, e.g., standard sequence comparison techniques, are also included in the invention. Unique conservative substitutions of disclosed peptide sequences are also included in this invention.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, "conservative amino acid substitutions", in one or a few amino acids in an amino acid sequence are substituted with different amino acids with highly similar properties, are also readily identified as being highly similar to a disclosed construct. Such conservative variations of each disclosed sequence are a feature of the present invention.

"Conservative variations" of a particular nucleic acid sequence refers to those nucleic acids which encode identical or essentially identical amino acid sequences (see, Table 1 below) or, where the nucleic acid does not encode the exact same an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid. Thus, "conservative variations" of a listed polypeptide sequence of the present invention include substitutions of a small percentage, typically less than 5%, more typically less than 2% or 1%, of the amino acids of the polypeptide sequence, with a conservatively selected amino acid of the same conservative substitution group. Finally, the addition of sequences which do not alter the encoded activity of a nucleic acid molecule, such as the addition of a non-functional sequence or sequences with accessory functions, is a conservative variation of the basic nucleic acid.

TABLE 1

Conservative Substitution Groups

| 1 | Alanine (A) | Serine (S) | Threonine (T) | |
|---|---|---|---|---|
| 2 | Aspartic acid (D) | Glutamic acid (E) | | |
| 3 | Asparagine (N) | Glutamine (Q) | | |
| 4 | Arginine (R) | Lysine (K) | | |
| 5 | Isoleucine (I) | Leucine (L) | Methionine (M) | Valine (V) |
| 6 | Phenylalanine (F) | Tyrosine (Y) | Trytophan (W) | |

In Table 1, substitution of an amino acid with another amino acid of the same group can be considered a conservative substitution.

Nucleic Acid Hybridization

Comparative hybridization can be used to identify nucleic acids of the invention, including conservative variations of nucleic acids of the invention. Comparative hybridization methods are preferred methods to distinguish nucleic acids of the invention. In addition, target nucleic acids which hybridize to the nucleic acids represented by SEQ ID NO: 1 or SEQ ID NO: 3 under stringent conditions, high, ultra-high and ultra-ultra high stringency conditions are a feature of the invention. Examples of such nucleic acids include those with one or a few silent or conservative nucleic acid substitutions as compared to a given nucleic acid sequence.

A test nucleic acid is said to specifically hybridize to a probe nucleic acid when it hybridizes at least ½ as well to the probe as to the perfectly matched complementary target, i.e., with a signal to noise ratio at least ½ as high as hybridization of the probe to the target under conditions in which the perfectly matched probe binds to the perfectly matched complementary target with a signal to noise ratio that is at least about 5×-10× as high as that observed for hybridization to any of the unmatched target nucleic acids.

Nucleic acids "hybridize" when they associate, typically in solution or on a solid support. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, New York), as well as in Ausubel, infra. Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection, and quantification of DNA and RNA, including oligonucleotides.

An example of stringent hybridization conditions for hybridization of complementary nucleic acids with about 50% GC content and having more than about 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see, Sambrook, infra for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

Wash conditions for "Stringent hybridizations" in the context of nucleic acid hybridization experiments such as Southern and northern hybridizations are sequence dependent, and are different under different environmental parameters. An extensive guide to the hybridization of nucleic acids is found in Tijssen (1993), supra. and in Hames and Higgins, 1 and 2. Stringent hybridization and wash conditions can easily be determined empirically for any test nucleic acid. For example, in determining highly stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria are met. For example, the hybridization and wash conditions can be gradually increased until a probe binds to a perfectly matched complementary target with a signal to noise ratio that is at least 5× as high as that observed for hybridization of the probe to an unmatched target.

"Very stringent" conditions can be selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-ultra-high stringency conditions.

Nucleic acids which do not hybridize to each other under stringent conditions are still substantially identical nucleic acids of the invention if the polypeptides which they encode are substantially identical. This can occur, e.g., when a copy of a nucleic acid is created using the maximum codon degeneracy permitted by the genetic code.

Unique Subsequences

In one aspect, the invention provides a nucleic acid which comprises a unique subsequence of a nucleic acid selected from the sequences of O-tRNAs and O-RSs disclosed herein, e.g., SEQ ID NO: 3 or SEQ ID NO: 1. The unique subsequence is unique as compared to a nucleic acid corresponding to any previously known O-tRNA or O-RS nucleic acid sequence, e.g., as found in Genbank. Alignment can be performed using, e.g., BLAST set to default parameters. Any unique subsequence is useful, e.g., as a probe to identify the nucleic acids of the invention.

Similarly, the invention includes a polypeptide which comprises a unique subsequence of a polypeptide selected from the sequences of O-RSs disclosed herein, e.g., SEQ ID NO: 2. Here, the unique subsequence is unique as compared to a polypeptide corresponding to any of known polypeptide sequence.

The invention also provides for target nucleic acids which hybridize under stringent conditions to a unique coding oligonucleotide which encodes a unique subsequence in a polypeptide selected from the sequences of O-RSs wherein the unique subsequence is unique as compared to a polypeptide corresponding to any of the control polypeptides. Unique sequences are determined as noted above, and as follows.

Sequence Comparison, Identity, and Homology

O-tRNAs, and O-RSs are considered translation components of the invention if, e.g., they share a certain homology (e.g., sequence identity) with component sequences of the invention. Product peptides of the translated according to methods of the invention having an amino acid sequence that is at least 75% identical, about 90% identical, about 95% identical, about 99% identical, or more, to that of a wild type therapeutic protein, a diagnostic protein, an industrial enzyme, or a portion thereof, and incorporating at least one unusual or unnatural amino acid residue are considered product peptides of the invention.

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill), or by visual inspection.

The phrase "substantially identical," in the context of two nucleic acids or polypeptides (e.g., DNAs encoding an O-tRNA or O-RS, or the amino acid sequence of an O-RS) refers to two or more sequences or subsequences that have at least about 60%, preferably 80%, most preferably 90-95% nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, "substantial identity" exists over a region of the sequences that is at least about 20 residues in length, about 50 residues in length, more preferably over a region of at least about 100 residues, and most preferably the sequences are substantially identical over at least about 150 residues, or over the full length of two compared sequences. The present invention includes nucleic acid sequences and amino acid sequences substantially identical to those disclosed herein for unique translation components of the invention.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores for nucleotide sequences are calculated using the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see, Henikoff & Henikoff (1989) *Proc. Natl. Acad. Sci. USA* 89:10915).

In addition to calculating percent sequence identity, the BLAST algorithm can also perform a statistical analysis of the similarity between two sequences (see, e.g., Karlin & Altschul, *Proc. Natl. Acad. Sci. USA* 90:5873-5787 (1993)).

One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001. Nucleic acids are considered similar to, and within the purview of the present invention, if they are similar to unique nucleic acids of the invention with smallest sum probability of than about 0.1, preferably less than about 0.01, and more preferably less than about 0.001.

Defining Polypeptides by Immunoreactivity

Because the polypeptides of the invention provide a variety of new polypeptide sequences (e.g., comprising 5-HTPP residues in the case of proteins synthesized in the translation systems herein, or, e.g., in the case of the novel synthetases, novel sequences of standard amino acids), the polypeptides also provide new structural features which can be recognized, e.g., in immunological assays. The generation of antisera, which specifically bind the polypeptides of the invention, as well as the polypeptides which are bound by such antisera, are a feature of the invention. For example, peptides of the invention include peptides immunoreactive with antibodies having specific binding affinity with peptides of the invention, as described above, but not significantly immunoreactive with other known peptides.

The term "antibody," as used herein, includes, but is not limited to a polypeptide substantially encoded by an immunoglobulin gene or immunoglobulin genes, or fragments thereof which specifically bind and recognize an analyte (antigen). Examples include polyclonal, monoclonal, chimeric, and single chain antibodies, and the like. Fragments of immunoglobulins, including Fab fragments and fragments produced by an expression library, including phage display, are also included in the term "antibody" as used herein. See, e.g., Paul, *Fundamental Immunology*, 4th Ed., 1999, Raven Press, New York, for antibody structure and terminology.

In order to produce antisera for use in an immunoassay, one or more of the immunogenic polypeptides is produced and purified as described herein. For example, recombinant protein can be produced in a recombinant cell. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, e.g., Harlow and Lane (1988) *Antibodies, A Laboratory Manual*, Cold Spring Harbor Publications, New York, for a standard description of antibody generation, immunoassay formats and conditions that can be used to determine specific immunoreactivity. Additional details on proteins, antibodies, antisera, etc. can be found in U.S. Ser. Nos. 60/479,931, 60/463,869, and 60/496,548 entitled "Expanding the Eukaryotic Genetic Code;" WO 2002/085923, entitled "IN VIVO INCORPORATION OF UNNATURAL AMINO ACIDS;" patent application entitled "Glycoprotein synthesis" filed Jan. 16, 2003, U.S. Ser. No. 60/441,450.

Methods of Incorporating Unnatural Amino Acids Into Peptides

Amino acids can be uniquely incorporated into peptides using the compositions and methods of the invention. Orthogonal transcription components of the invention can be engineered and inserted into endogenous transcription systems. The orthogonal components can introduce a natural or unnatural amino acid into unusual positions of a growing peptide chain. The resultant peptide can have unique properties useful in fields of technical endeavor, such as medicine, analysis, biological research, industrial processing, and the like.

Incorporation of an amino acid into an unusual position can include incorporation of natural or unnatural amino acids into peptides at positions not provided in standard codon translation. Incorporation into an unusual position can include, e.g., incorporation of a natural amino acid in a position normally encoding (i.e., according to the 61 standard translation codons) a different natural amino acid. That is, a standard codon triplet can act as a selector codon for certain unusually charged O-tRNAs. Incorporation of a natural or unnatural amino acid can also be in response to a normally non-coding codon, such as a termination codon, unnatural codon, 4-base codon, etc. Incorporation of an unnatural amino acid into any position of a peptide can be considered incorporation into an unusual position.

An amino acid can be incorporated at an unusual position in a protein, e.g., by preparing a construct of an orthogonal aminoacyl-tRNA synthetase (O-RS) of the invention, preparing a construct of an orthogonal tRNA (O-tRNA) of the invention, transfecting the constructs into a cell, expressing the constructs to provide O-RS and O-tRNA, adding the O-RS and O-tRNA to an endogenous translation system, charging the O-tRNA using the O-RS, and translating an mRNA having a codon complimentary to the anticodon of the O-tRNA to incorporate an amino acid into a protein at an unusual position. The construct expression products can be purified and added to an endogenous translation system in vitro or expressed in a living cell with an endogenous in vivo translation system. The O-RS of the invention can charge the O-tRNA with a natural or unnatural amino acid. The anticodon of the O-tRNA can be complimentary to a nonstandard selector codon or to a selector codon normally assigned to an amino acid different from the one charged onto the O-tRNA by the O-RS.

Methods for generating and selecting O-tRNAs, O-RSs, and orthogonal pairs have been described, e.g., in U.S. patent application Ser. No. 10/126,927, "In Vivo Incorporation of Unnatural Amino Acids", by Shultz, et al., and U.S. application Ser. No. 10/126,931, "Methods and Compositions for the Production of Orthogonal tRNA-Aminoacyl tRNA Synthetase Pairs", by Shultz, et al., which are incorporated into this document by reference. For example, a recombinant orthogonal aminoacyl-tRNA synthetase (O-RS) of the invention can be produced by generating a library of (optionally mutant) RSs derived from at least one aminoacyl-tRNA synthetase (RS) from a first organism, selecting (and/or screening) the library of RSs to provide a pool of active RSs that aminoacylate an orthogonal tRNA (O-tRNA), and screening the pool for active RSs that preferentially aminoacylate the O-tRNA in the presence of an unnatural amino acid. In another example, a recombinant orthogonal tRNA (O-tRNA) of the invention can be produced by generating a library of mutant tRNAs derived from at least one tRNA, selecting or screening the library for tRNAs that are aminoacylated by an aminoacyl-tRNA synthetase (RS) from a second organism in the absence of an RS from the first organism to provide a pool of functional tRNAs, and selecting or screening the pool of tRNAs for members that are aminoacylated by an introduced orthogonal RS (O-RS) to provide at least one recombinant O-tRNA that, e.g., recognizes a selector codon, is not efficiently recognized by the RS from the second organism, and is preferentially aminoacylated by the O-RS. Such O-tRNAs and O-RSs of the invention can be provided, e.g., in complimentary O-tRNA/O-RS pairs of the invention that function in concert with an endogenous translation system to specifically and efficiently incorporate unnatural amino acids into a peptide of the invention.

Mutagenesis and Other Molecular Biology Techniques

Polynucleotides and polypeptides of the invention can be prepared and manipulated using molecular biological techniques. General texts which describe molecular biological techniques include Berger and Kimmel, *Guide to Molecular Cloning Techniques, Methods in Enzymology volume* 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2001 ("Sambrook") and *Current Protocols in Molecular Biology*, F. M. Ausubel et al., eds., *Current Protocols*, a joint venture between Greene Publishing Associates, Inc. and John Wiley & Sons, Inc., (supplemented through 2003) ("Ausubel")). These texts describe mutagenesis, the use of vectors, promoters and many other relevant topics related to, e.g., the generation of genes that include selector codons for production of proteins that include tryptophan derivatives, orthogonal tRNAs, orthogonal synthetases, and pairs thereof.

Various types of mutagenesis can be used in the invention, e.g., to mutate tRNA molecules, to produce libraries of tRNAs, to mutate synthetases, to produce libraries of synthetases, and/or to insert selector codons into nucleic acids encoding proteins or polypeptides of interest. Mutagenesis techniques include, but are not limited to, site-directed mutagenesis, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure, or the like.

Host cells can be genetically engineered (e.g., transformed, transduced or transfected) with the polynucleotides of the invention or constructs which include a polynucleotide of the invention, e.g., a vector of the invention, which can be, for example, a cloning vector and/or an expression vector. For example, the coding regions for the orthogonal tRNA, the orthogonal tRNA synthetase, and the protein to incorporate an unusual amino acid can be operably linked to gene expression control elements that are functional in the desired host cell. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both (e.g., shuttle vectors), and selection markers for both prokaryotic and eukaryotic systems. Vectors are suitable for replication and/or integration in prokaryotes, eukaryotes, or preferably both. See Giliman & Smith, *Gene* 8:81 (1979); Roberts, et al., *Nature*, 328:731 (1987); Schneider, B., et al., *Protein Expr. Purif.* 6435:10 (1995); Ausubel, Sambrook, Berger (all supra). The vector can be, for example, in the form of a plasmid, a bacterium, a virus, a naked polynucleotide, or a conjugated polynucleotide. The vectors can be introduced into cells and/or microorganisms by standard methods including, e.g., electroporation (From et al., *Proc. Natl. Acad. Sci. USA* 82, 5824 (1985)), infection by viral vectors, high velocity ballistic penetration by small particles with the nucleic acid either within the matrix of small beads or particles, or on the surface (Klein et al., *Nature* 327, 70-73 (1987)), and/or the like.

A catalogue of bacteria and bacteriophages useful for cloning is provided, e.g., by the ATCC, e.g., *The ATCC Catalogue of Bacteria and Bacteriophage* (1996) Gherna et al. (eds) published by the ATCC. Additional basic procedures for sequencing, cloning and other aspects of molecular biology and underlying theoretical considerations are also found in Sambrook (supra), Ausubel (supra), and in Watson et al. (1992) *Recombinant DNA Second Edition Scientific American Books, NY*. In addition, essentially any nucleic acid (and virtually any labeled nucleic acid, whether standard or non-standard) can be ordered from any of a variety of commercial sources, such as the Midland Certified Reagent Company (Midland, Tex. mcrc.com), The Great American Gene Company (Ramona, Calif. available on the World Wide Web at genco.com), ExpressGen Inc. (Chicago, Ill. available on the World Wide Web at expressgen.com), Operon Technologies Inc. (Alameda, Calif.) and many others.

The engineered host cells can be cultured, in conventional nutrient media modified as appropriate for such activities as, for example, screening steps, activating promoters or selecting transformants. These cells can optionally be cultured into transgenic organisms. Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

Preparing O-RS Constructs

Orthogonal aminoacyl-tRNA synthetase constructs of the invention can be engineered with a variety of elements appropriate to the desired expression systems, selection systems, and/or translation systems. An O-RS construct can include, e.g., a plasmid vector with an appropriate promoter and selectable marker. Sequences of the constructs encoding the O-RS protein can include mutations that enhance the amino acid specificity, tRNA specificity, enzymatic activity, and/or fidelity of the expressed enzyme. The expressed construct can be, e.g., a chimera including purification tags and detectable markers.

In general, O-RSs of the invention can be expressed using a plasmid comprising a nucleic acid sequence encoding the O-RS, a promoter to initiate expression, and a sequence for a selectable marker that maintains the plasmid in the cell. The promoter can be a DNA sequence including a site of transcription initiation compatible with RNA polymerases of the expression cell type. The promoter can be highly active and inducible. A promoter commonly used in prokaryotic expression systems is the lac promoter. Promoters commonly used in mammalian cell expression systems include the CMV promoter and the human cell EF-1α promoter. Selectable markers encoded by expression vectors can stabilize a plasmid against elimination from a cell host and provide a way to identify cells harboring the vector. A positive selective marker can be, e.g., an antibiotic resistance gene so that only host cells transformed with the vector can grow in media containing the antibiotic. A negative selector, such as an inducible toxin can identify cell clones harboring the vector as those that die or fail to thrive in the presence of the toxin inducing agent.

It is often convenient to include a reporter sequence in the construct to aid in the detection and quantitation of the vector and/or the expressed protein. Typically, a detectable marker peptide sequence is fused to the O-RS sequence so that the presence and amount of O-RS expression can be inferred. For example, a fluorescent green protein (FGP) sequence can be fused to an O-RS sequence of the invention for detection of expressed fusion protein by a characteristic fluorescent excitation/emission profile. Another way to conveniently detect and quantitate expressed O-RS is to fuse the sequence with an antigen sequence (such as a FLAG or V5 sequence) for analysis of the expressed fusion protein by, e.g., western blot analysis.

In cases where convenient purification of expressed O-RS of the invention is desirable, the sequence can include a purification tag that allows the protein to be separated from other biomolecules using a specific affinity. For example, a his6 tag with affinity for chelated nickel, or an antigen tag bound by an antibody can be used, e.g., in an affinity chromatography column format to rapidly purify the expressed protein. Purified O-RS/tag fusion protein can then be subjected to analysis, such as, e.g., mass spectroscopy, or added to a translation system.

O-RSs of the invention can be obtained, e.g., by screening techniques, random mutation, directed mutation, and/or the like. A foreign RS can be an O-RS when added to an endogenous translation system. For example, an RS from a prokaryotic organism can function as an O-RS in the endogenous translation system of a eukaryotic organism. Optionally, a foreign or native RS can be subjected to random mutation techniques known in the art and screened for O-RS functionality, e.g., with O-tRNAs and/or unnatural amino acids. More typically, available structural information, particularly at the RS active site, can be used to make an intelligent appraisal of amino acid positions most likely to influence the activity and specificity of the RS interactions with aminoacylated tRNAs of interest. For example, based on x-ray crystallography data on the RS, or an analogous RS, inferences can be made as to amino acid residue positions that can interfere with or facilitate functional fitting and interactions with a particular aminoacylated tRNA. In one embodiment, for example, an orthogonal (O-RS/O-tRNA) pair that functions to charge with one amino acid can be mutated to charge a larger (e.g., derivatized) amino acid or differently charged amino acid by site directed mutations. An O-RS amino acid residue identified from crystallography data as extending into the active site can be specifically mutated to exchange it for, e.g., an amino acid with a shorter side chain to reduce steric hindrance in the active site and improving the fit of the larger amino acid in the active site. Optionally, one or more identified amino acid residues associated with RS activity and/or specificity can be mutated to provide, e.g., RSs with each of the 19 alternative natural amino acids (or, optionally unnatural amino acids) for screening and identification of the optimum mutation(s) for the desired function.

Orthogonal tryptophanyl-tRNA synthetases (O-TrpRS), particularly prokaryotic tryptophanyl-tRNA synthetases, are preferred in embodiments of O-RS constructs in the invention. Orthogonal mutant tryptophanyl-tRNA synthetases (O-muTrpRS) are preferred in O-RS constructs of the invention. In one example, O-muTrpRS constructs of the invention are derived from prokaryotic TrpRSs through site directed mutations of amino acids located at the active site of the enzyme.

In a preferred embodiment of this example, the O-muTrpRS is a *Bacillus subtilis* TrpRS mutated at Val144, mutated Val144Pro, or derivatives thereof. For example, the O-muTrpRS can be encoded by the nucleotide encoding Val144ProBsTrpRS (i.e., SEQ ID NO: 1), a complimentary sequence, or a conservative variation thereof. Most preferred O-muTrpRSs include, e.g., those having the amino acid sequence of Val144ProBsTrpRS (i.e., SEQ ID NO: 2) or conservative substitutions thereof.

Screening O-RS Constructs

O-RS constructs of the invention can be expressed in in vitro translation systems or in vivo translation systems (e.g., in living cells) to screen for desired activity and/or specificity. In cases where there is a high degree of confidence in the protein design engineering, or where a construct has previously been characterized, the construct can be transduced, transformed, or transfected into host cells for expression and production of the O-RS (and/or O-tRNA) of the invention. In many cases a library of alternate candidate constructs is prepared, e.g., for a series of expression, screening, and selection steps to identify the constructs with characteristics desirable in a particular orthogonal transcription subsystem.

Several well-known methods of introducing target nucleic acids into bacterial cells are available, any of which can be used in the present invention. These include: fusion of the recipient cells with bacterial protoplasts containing the DNA, electroporation, projectile bombardment, infection with viral vectors, and/or the like. Bacterial cells can be used to amplify the number of plasmids containing DNA constructs of this invention. The bacteria can be grown to log phase and plasmid vectors replicated within the bacteria can be isolated by a variety of methods known in the art (see, for instance, Sambrook). In addition, a plethora of kits are commercially available for the purification of plasmids from bacteria, (see, e.g., EasyPrep™, FlexiPrep™, both from Pharmacia Biotech; StrataClean™, from Stratagene; and, QIAprep™ from Qiagen). The isolated and purified plasmids can then be, e.g., further manipulated to produce other plasmids, used to transfect cells, or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for prokaryotic and/or eukaryotic systems. Vectors can be suitable for replication and integration in prokaryotes, eukaryotes, or preferably both. See, Giliman & Smith, *Gene* 8:81 (1979); Roberts, et al., *Nature,* 328:731 (1987); Schneider, B., et al., *Protein Expr. Purif.* 6435:10 (1995); Ausubel, Sambrook, Berger (all supra). A catalogue of Bacteria and Bacteriophages useful for cloning is provided, e.g., by the ATCC, e.g., *The ATCC Catalogue of Bacteria and Bacteriophage* (1992) Gherna et al. (eds.) published by the ATCC. Additional basic procedures for sequencing, cloning and other aspects of molecular biology and underlying theoretical considerations are also found in Watson et al. (1992) *Recombinant DNA Second Edition* Scientific American Books, NY.

Screening or selecting of RS candidate enzymes for a desired O-RS function can involve, e.g., introduction of the candidate into an in vivo translation system in the form of expression vector DNA, or into an in vitro translation system in the form of an mRNA or peptide. RS candidates can be preliminarily screened for the presence of any aminoacylation activity with a prospective tRNA orthogonal pair member to provide a library of active RSs. A library of active RSs can be screened, e.g., by detection of a marker protein that can only be expressed in the presence of an appropriate functioning O-RS. For example, a marker protein can comprise a selectable marker and/or a detectable marker. The marker protein can provide, e.g., cell viability (e.g., antibiotic resistance), cell toxicity or death (e.g., toxin proteins), a fluorescent signal (e.g., fluorescent proteins), antigens detectable in sandwich assays, and/or the like. The nucleic acid sequence for the marker protein can include a selector codon, e.g., not translated as the desired amino acid by the endogenous translation system, so that a functional marker protein is only expressed if the active RS charges a tRNA having the complimentary anticodon. False positive results, where the active RS charges the selector codon complimentary tRNA with the wrong amino acid can be detected and eliminated, e.g., by observation of unusual marker protein function, or qualitative analysis (such as, e.g., electrospray ionization mass spectroscopy) of the marker protein product.

O-RSs that have been screened for proper function can be further tested to select O-RSs of the invention having improved desired specificity. For a mutant O-RS derived from an RS that normally charges a paired tRNA with a first amino acid, and which charges the tRNA with a second (optionally unnatural) amino acid, the mutant O-RS can be tested for preferential aminoacylation of a paired tRNA with the second amino acid over the first amino acid. For example, a translation system including the mutant RS can be tested for expression of a marker protein with and without the second amino acid. If the marker protein is expressed in a translation system not containing the second amino acid, the mutant RS may be, e.g., charging the paired tRNA with the first amino acid. If the marker protein is expressed full length in the presence of the second amino acid, and only in a shortened form without the second amino acid, the mutant RS may be, e.g., preferentially aminoacylating the tRNA with the second amino acid over the natural amino acids of the endogenous translation system. Marker proteins expressed in a translation system having added mutant RS and second amino acid can be analyzed (e.g., by electrospray ionization mass spectroscopy or western blotting) to detect the presence and/or proportion of translation errors resulting from, e.g., inconsistent charging of the paired tRNA by the mutant RS. Although inconsistent charging by O-RSs of the invention can be acceptable to some degree, it is preferred that O-RSs preferentially aminoacylate their paired tRNA with the desired amino acid. For example, O-RSs of the invention can preferentially aminoacylate their paired tRNA (optionally O-tRNA) with the intended (optionally unnatural) amino acid in a proportion greater than 1 to 1, about 2 to 1, about 4 to 1, about 5 to 1, about 20 to 1, about 100 to 1, or more, over charging with unintended (typically natural) amino acids.

O-RSs that have been screened for proper function can be further tested to select O-RSs having adequate activity. O-RSs added to an endogenous translation system with their paired tRNA can incorporate cognate amino acid (typically unnatural) into a peptide at a rate similar to endogenous amino acid incorporation under similar conditions. The activity of an O-RS can be measured, e.g., by detecting incorporation of radioactive cognate amino acid into a peptide, quantitation of associated expression product by SDS-PAGE, and the like. Activity can be compared to endogenous expression levels of, e.g., analogous proteins. In the present invention, O-RSs can have activities, e.g., about 1%, about 5%, about 10%, about 25%, about 50%, about 80%, about 90%, about 100%, or more, of typical endogenous (optionally analogous) RSs. For example, the expression of a wild type protein can be compared to the expression of a protein (e.g., alloprotein) encoded by the wild type sequence mutated to include a selector codon. Alternately, the Km and/or Kcat of O-RSs can be evaluated empirically, according to methods known in the art, to determine the activity of an O-RS. In a preferred embodiment, O-RSs (e.g., from mutated, screened, and/or previously selected libraries of RSs) of the invention are selected based on improved or enhanced enzymatic properties, such as, e.g., Km and Kcat, for an unnatural amino acid as compared to a natural amino acid.

Should screening and selection of O-RS candidates fail to provide an O-RS with the desired activity and/or specificity, the search can continue with additional rounds of obtaining foreign RSs, protein design, mutation, screening, and/or selecting.

Preparing O-tRNA Constructs

O-tRNAs of the invention can be expressed from DNA constructs created by recombinant techniques similar to those described above. However, tRNAs are expressed as ribonucleic acids that are not ultimately translated into a peptide. O-tRNA constructs, and RNA expression products have special considerations not found in constructs for expression of proteins. For example, tRNA sequences are transcribed by a special RNA polymerase (RNA polymerase III) different from the RNA polymerase that transcribes mRNAs.

O-tRNA sequences of the invention can have a variety of elements that can influence expression, activity, and specificity. For example, in many cases, an O-tRNA of the invention can be derived from a tRNA foreign to the endogenous translation system. tRNAs in eukaryotes are transcribed by RNA polymerase III which recognizes two conserved intragenic transcriptional control elements, the A box and the B box. A eukaryotic RNA polymerase III may not effectively recognize initiation signals of a prokaryotic tRNA sequence. In such a case, e.g., nucleic acid residues in the D arm of the tRNA can be mutated to code an "A box" 15 segment recognized by a eukaryotic RNA polymerase III, e.g., as shown in FIG. 1. Expression of some tRNA genes in eukaryotes can also depend upon the presence of certain 5' flanking sequences. For example, expression of tRNA$^{Trp}$ in eukaryotes can require 5' flanking sequences which are distinctly AT rich and contain several possible TATA elements. Such sequences can be included in O-tRNA constructs of the invention to enhance expression efficiency. Another useful expression element in O-tRNA constructs of the invention can be a properly positioned terminator element in the 3' flanking sequence. Such a sequence can be derived, e.g., from a 3' flanking sequence used by the endogenous translation system source organism, or an analogous organism.

O-tRNA constructs of the invention typically include a mutation in the anticodon loop, e.g., providing recognition of a selector codon. In one aspect of the invention, the anticodon is complimentary to one of the 61 codons (preferably a rare codon) that normally designate one of the 20 natural amino acids, yet the O-tRNA is charged with a different (unusual, e.g., unnatural) amino acid. In a preferred embodiment, the anticodon of the O-tRNA is complimentary to a selector codon, such as, e.g., a unique three base codon, a nonsense codon, such as a stop codon, e.g., an amber codon, or an opal codon, an ochre codon, an unnatural codon, a codon with unnatural bases, a four (or more) base codon, and/or the like. For example, the O-tRNAs of the invention can be suppressors with anticodons such as, e.g., UCA, UUA, or CUA. In a preferred embodiment, the O-tRNA has a UCA opal suppressor anticodon.

O-tRNAs of the invention can be, e.g., preferentially aminoacylated by a paired complimentary O-RS of the invention. That is, e.g., the O-RS preferentially charges the O-tRNA over endogenous tRNAs of the endogenous translation system. The O-tRNA can be mutated to be a preferred substrate for the O-RS. More commonly, the O-RS/O-tRNA pair of the invention is obtained from the same or analogous translation system foreign to the endogenous translation system. Being from the same or similar (e.g., analogous) translation system, the pair members tend to interact specifically with each other. In some cases, the O-RS is mutated to retain specificity for the O-tRNA in response to mutations introduced into the O-tRNA, e.g., to allow expression in the endogenous system, or to provide preferential charging with a different amino acid. In another embodiment, preferential aminoacylation by an O-RS can be obtained by screening a library of O-tRNAs to identify a preferred substrate for the O-RS, e.g., in combination with an amino acid of interest. Such screening can be practiced in a fashion similar to screening methods described above for O-RS screening, or by other screening methods known in the art. It is preferred that O-tRNAs of the invention be preferentially aminoacylated by their paired O-RS with the desired amino acid, e.g., in a proportion greater than 1 to 1, about 2 to 1, about 4 to 1, about 5 to 1, about 20 to 1, about 100 to 1, or more, over charging of other tRNAs, such as endogenous tRNAs.

The tRNA of the invention charged with unusual amino acids is preferably an orthogonal tRNA charged with tryptophan, an amino acid derived from tryptophan, or a tryptophan analog. The O-tRNA of the invention can be, e.g., a tRNA$^{Trp}$, an orthogonal mutant tRNA$^{Trp}$ (O-mu tRNA$^{Trp}$), or an orthogonal mutant tRNA$^{Trp}$ with a suppressor anticodon, such as, e.g., mutRNA$_{UCA}^{Trp}$. In a preferred embodiment, the mutRNA$_{UCA}^{Trp}$ is derived from a *Bacillus* species, such as *Bacillus subtilis* or *Bacillus stearothermophilus*. In a most preferred embodiment, the construct encodes the O-tRNA sequence 5'AGGGGCGUGGCUUAACGGUAGAGCA-GAGGUCUUCAAAACCUCCGGUGUGG GUUCGA-UUCCUACCGCCCCUG 3' (SEQ ID NO: 3), a complementary polynucleotide sequence, or a conservative variation. Optionally, the construct of the invention can encode a conservative variation of SEQ ID NO: 3 that recognizes a selector codon or a polynucleotide sequence which hybridizes under highly stringent conditions over substantially the entire length of the polynucleotide sequence (SEQ ID NO: 3).

O-tRNA constructs of the invention can be replicated and/or expressed by introduction into a living cell. Methods to introduce genetic constructs into cells are well known, and discussed above, e.g., in the "Preparing O-RS Constructs" section. In a preferred embodiment, the cell is a transfected eukaryotic cell. In a more preferred embodiment, the eukaryotic cell is a mammalian cell, such as a human cell line.

Incorporating an Unnatural Amino Acid into a Peptide

O-RSs of the invention can charge paired O-tRNAs with unusual (typically unnatural) amino acids that can be incorporated into a peptide encoded with a codon complimentary to the O-tRNA anticodon. The unnatural amino acids can affect the character of the resultant alloprotein. The alloprotein can have unique qualities useful as therapeutics, diagnostics, in industrial processing, materials sciences, nanotechnologies, computer sciences, electronics, and/or the like.

Nucleic acid constructs for expression of an alloprotein of the invention can be recombinantly engineered, e.g., using restriction endonucleases, DNA synthesizers, vectors, and host cells as described above in the Preparing O-RS Constructs section. The alloprotein construct can be a vector having functional coding for initiation of replication, selectable markers, detection markers, initiation of transcription, and the like. The alloprotein coding sequence can include one or more selector codons, e.g., designating a position for incorporation of an unusual (e.g., unnatural) amino acid. The alloprotein construct can incorporate, e.g., coding sequences for an O-RS, an O-tRNA in the same vector for co-transfection and expression. Optionally, sequences for orthogonal translation components of the invention can be present on separate vector constructs.

An alloprotein construct of the invention can be introduced into a living cell for translation in vivo. In such a case, the unnatural amino acid can often be supplied as a supplement to a media in which the cell is cultured. For example, a mammalian cell, transfected with a vector containing coding sequences for an orthogonal pair and an alloprotein of the invention can be grown in minimal essential media containing 1 mM of the appropriate cognate unnatural amino acid for translation of the alloprotein with incorporation of the unnatural amino acid. Unnatural amino acids of the invention are generally alpha-amino acids capable of acting as substrates in aminoacylation of a tRNA and peptide bond formation during translation of a nucleic acid sequence into a peptide sequence. The unnatural amino acids can be synthesized, e.g., by chemical processes in vitro and/or biologically synthesized in a cell. In many cases, as described above, unnatural amino acids are derivatives of natural amino acids. For example, chemical groups can be chemically or enzymatically added to natural amino acids to provide, e.g., a functional group, linker, ionic charge, hydrophobic group, coordination structure, affinity group, detectable marker, radioactive label, and/or the like, on the amino acid (and, ultimately, in an alloprotein). In one aspect of methods of the invention, the unnatural amino acid is a tryptophan derivative, such as 5-HTPP, and the orthogonal pair is an O-mu TrpRS and a O-tRNA functioning to incorporate the tryptophan derivative at a position designated by a nonsense mutation selector codon in a expression protein construct.

In vitro translation can be accomplished, e.g., by simply adding the orthogonal components of the invention directly into a solution containing an endogenous translation system, for incorporation of the unnatural amino acid into the peptide. The orthogonal components can be unpurified, partially purified, or highly purified before addition to the in vitro endogenous translation system. For example, affinity purified O-RS (from a construct including a purification tag), O-tRNA from a total tRNA prep, a chemically modified and crystallized unnatural amino acid, and a poly-T purified total mRNA prep, can be added in appropriate amounts to a wheat germ lysate translation system for production of a full length alloprotein in vitro (often in a container, such as an Eppendorf tube).

Endogenous translation systems contain, e.g., all the components necessary to translate an mRNA nucleic acid into a full length peptide sequence containing the 20 common natural amino acids. Orthogonal translation components of the invention, such as O-RSs, O-tRNAs, genes for proteins with internal codons not read correctly by the translation system, and/or unnatural amino acids, can be added to the endogenous translation system to obtain translation products not available from the endogenous translation system alone. For example, a gene encoding 40 amino acid peptide with a nonsense mutation at the codon for amino acid 21 will be expressed in an endogenous translation system as a 20 amino acid peptide fragment. A 40 amino acid full length alloprotein of interest can be expressed with an unnatural amino acid at position 21 by addition of the unnatural amino acid and an appropriate orthogonal pair of the invention into the translation system.

The incorporation of unnatural amino acids such as 5-HTPP in vivo can be done without significant perturbation of the host cell. For example, in non-eukaryotic cells, such as *Escherichia coli*, because the suppression efficiency a stop selector codon, e.g., the UCA codon, can depend on the competition between an O-tRNA (e.g., an opal suppressor tRNA) and a release factor (RF) that binds to the UCA codon and initiates release of the growing peptide from the ribosome, the suppression efficiency can be modulated by, e.g., either increasing the expression level of O-tRNA, or using an RF deficient strain. In eukaryotic cells, because the suppression efficiency for a UCA codon can depend on the competition between the O-tRNA and a eukaryotic release factor (e.g., eRF), the suppression efficiency can be modulated by, e.g., increasing the expression level of O-tRNA. Additional compounds can also be present to modulate release factor action, e.g., reducing agents such as dithiothretiol (DTT).

In one aspect of the invention, a composition includes at least one protein with at least one, e.g., at least two, at least three, at least four, at least five, at least six, at least seven, at least eight, at least nine, at least ten, or more unusual amino acids, e.g., amino acids encoded non-standardly, tryptophan analogs, derivatives, and/or other unnatural amino acids. The unusual and/or unnatural amino acids can be the same or different, e.g., there can be 1, 2, 3, 4, 5, 6, 7, 8, 9, or 10, or more different sites in the protein that comprise 1, 2, 3, 4, 5, 6, 7, 8, 9, or 10 or more different unusual or unnatural amino acids. In another aspect, a composition includes a protein with at least one, but fewer than all, of a particular amino acid present in the protein is substituted with a tryptophan derivative. For a given protein with more than one unnatural amino acid, the unnatural amino acids can be identical or different (e.g., the protein can include two or more different types of unnatural amino acids, or can include two of the same unnatural amino acid). For a given protein with more than two unnatural amino acids, the unnatural amino acids can be the same, different or a combination of a multiple unnatural amino acid of the same kind with at least one different unnatural amino acid.

Nucleic acids encoding product peptides of the invention can be expressed, e.g., in a translation system of a cell to provide product proteins that comprise unnatural or unusual amino acids in large useful quantities. In one aspect, the composition optionally includes, e.g., at least 10 micrograms, at least 50 micrograms, at least 75 micrograms, at least 100 micrograms, at least 200 micrograms, at least 250 micrograms, at least 500 micrograms, at least 1 milligram, at least 10 milligrams, or more of the protein that comprises a 5-HTPP residue, or an amount that can be achieved with in vivo protein production methods (details on recombinant protein production and purification are provided herein). In another aspect, the protein is optionally present in the composition at a concentration of, e.g., at least 10 micrograms of protein per liter, at least 50 micrograms of protein per liter, at least 75 micrograms of protein per liter, at least 100 micrograms of protein per liter, at least 200 micrograms of protein per liter, at least 250 micrograms of protein per liter, at least 500 micrograms of protein per liter, at least 1 milligram of protein per liter, or at least 10 milligrams of protein per liter, or more, in, e.g., a cell culture media, a cell lysate, a buffer, a pharmaceutical buffer, or other liquid suspension (e.g., in a volume of, e.g., anywhere from about 1 nL to about 100 L, or more). The production of large quantities (e.g., greater than that typically possible with other methods, e.g., in vitro translation) of a protein in a cell including at least one 5-HTPP is a feature of the invention.

Using Alloproteins Having Incorporated Tryptophan Derivatives

Modified expression of a protein, including incorporation of unnatural amino acids, by methods of the invention can provide, e.g., useful products in the fields of medicine, analyses, manufacturing, and processing. Therapeutic proteins can be engineered, e.g., to have improved bioavailability, reduced toxicity, improved stability, novel activity, enhanced activity, linkage options, improved traceability, and/or the like. Diagnostic proteins can have, e.g., new opportunities for linkage chemistries, more specific linkage to markers, stronger signals, improved resolution from other proteins, and/or the like. Industrial enzymes can be improved, e.g., with new activities, increased activities, enhanced stability, improved linkages to catalytic surfaces, modified substrate specificity, and/or the like.

Incorporation of 5-HTPP into a peptide can provide unique fluorescent signals for sensitive detection and accurate measurement of the peptide product in complex or purified mixtures. 5-HTPP has fluorescent excitation and emissions maxima significantly shifted from those of tryptophan. For example, a peptide with a tryptophan residue can have a fluorescent emissions maximum at $\lambda_{max}$ of 367 nm, but emissions with the tryptophan exchanged for 5-HTPP can be, e.g., at 334 nm. A more than 10-fold difference in emissions can be observed between a natural and 5-HTPP modified peptide. Careful adjustment of the excitation wavelength can be used to further accentuate the difference in emissions. Using these and other techniques of the invention, proteins incorporating 5-HTPP can be observed against a background of tryptophan fluorescence from other proteins or from tryptophans in the modified peptide itself.

In another aspect, a peptide having an incorporated 5-HTPP can be used as a probe to detect certain interactions. For example, a peptide can be modified to incorporate 5-HTPP in a region of interest in the peptide chain. Interactions of the region with, e.g., other proteins or cell membranes can be detected as shifts or quenching of the 5-HTPP fluorescence.

Incorporating 5-HTPP into peptides can provide opportunities for unique linker chemistries. Incorporated 5-HTPP in solution can undergo redox chemistry in the presence of electric potentials to afford a reactive tryptophan-4,5-dione. The reactive group can form covalent bonds with other reactive molecules, e.g., for attachment of linker groups or detectable markers to the peptide. Optionally, 5-HTPP modified peptides can be cross-linked under the influence of suitable electrical potentials. In a preferred embodiment, the timing of linker reactions is controlled by providing a suitable pH and exerting an appropriate voltage, e.g., 400 mV to about 1000 mV on a solution containing the modified peptide.

EXAMPLES

The following examples are offered to illustrate, but not to limit the claimed invention. It is understood that the examples and embodiments described herein are for illustrative purposes only and that various modifications or changes in light thereof will be suggested to persons skilled in the art and are to be included within the spirit and purview of this application and scope of the appended claims.

Example

Orthogonal Incorporation of 5-HTTP into a Peptide

An orthogonal tryptophanyl-tRNA synthetase (O-TrpRS)-opal suppressor (mu tRNA$_{UCA}^{Trp}$) pair was generated for use in mammalian cells. The anticodon loop of a *Bacillus subtilis* tRNA$^{Trp}$ was mutated to UCA, three positions in the D-arm were mutated to generate an internal promoter sequence, and the mutRNA$_{UCA}^{Trp}$ gene was inserted between the 5' and 3' flanking sequences of the tRNA$^{Trp1}$ gene from *Arabidopsis* to enhance its expression in mammalian cells. In vitro aminoacylation assays and in vivo opal suppression assays showed that *B. subtilis* TrpRS (BsTrpRS) charged the cognate mu tRNA$_{UCA}^{Trp}$ and no endogenous tRNAs of the endogenous mammalian translation system. Similarly, the mu tRNA$_{UCA}^{Trp}$ was specifically charged by *B. subtilis* TrpRS and not by endogenous synthetases in mammalian cells. Site-directed orthogonal mutagenesis was then used to alter the specificity of BsTrpRS to uniquely charge 5-hydoxy-L-tryptophan (5-HTTP). The resulting mutant BsTipRS-mutRNA$_{UCA}^{Trp}$ orthogonal pair allowed efficient and selective incorporation of 5-HTPP into a mammalian protein in response to the codon, TGA. This amino acid can be incorporated into unique fluorescence probe peptides and/or into peptides to act as an in situ protein cross-linking agent.

Materials and Methods

General.

Mammalian cells were transfected with Fugene 6 reagent (Roche). Radio-labeled amino acids were obtained from Perkin Elmer (Boston, Mass.) and oligonucleotides were from Proligo (La Jolla, Calif.). Genomic DNAs were obtained from ATCC (Manassas, Va.). Antibodies, antibiotics and TRIZOL solution were purchased from Invitrogen (Carlsbad, Calif.). V5-antibody-immobilized agarose was purchased from Bethyl Laboratories, Inc. (Montgomery, Tex.). 5-Hydroxy-L-tryptophan was from Sigma (St. Louis, Mo.) and used without further purification. Nucleobond columns were purchased from Clontech (Palo Alto, Calif.).

Strains.

*E. coli* strains DH10B and TOP10 were used for plasmid propagation and isolation. Human kidney 293T cells were used for unnatural amino acid incorporation into proteins.

Plasmids.

The DNA fragment encoding *B. subtilis* TrpRS (BsTrpRS) was amplified from genomic DNA by polymerase chain reaction (PCR) and cloned into the XhzoI-PacI sites of the pMH4 vector (GNF, La Jolla, Calif.). The resulting plasmid pMHTrpRS was used to express BsTrpRS with a His6 purification tag at the N-terminus in *E. coli*. To express BsTrpRS in mammalian cells, the PCR fragment encoding the synthetase was ligated into a pEF6-V5-His6-TOPO vector (Invitrogen, Carlsbad, Calif.). The resulting plasmid pEF6-TrpRS encodes wild-type *B. subtilis* TrpRS with C-terminal V5 and His6 epitope tags. A series of mutant synthetases was generated in this vector by site-directed mutagenesis using QuikchangeXL (Stratagene, La Jolla, Calif.) and mutagenic primers.

The suppressor mutRNA$_{UCA}^{Trp}$ gene was constructed by annealing two oligodeoxynucleotides. The first encodes the corresponding mutRNA$_{UCA}^{Trp}$ sequence fused to the 5'-flanking sequence (AAAATTAATTAAACGTTTA-GAAATATAGATGAACT TTATAGTACAA, SEQ ID NO:5) of the tRNA$^{Trp1}$ gene. The second oligonucleotide consisted of the corresponding mu tRNA$_{UCA}^{Trp}$ fused to the 3'-flanking sequence GTCCTTTTTTTG (SEQ ID NO:6). Klenow fragment was used to generate a duplex DNA which was inserted into the PstI and XhoI sites of pZeoSV2(+) (Invitrogen, Carlsbad, Calif.). The resulting plasmid pTrptRNA was used to transcribe mu tRNA$_{UCA}^{Trp}$ in mammalian cells.

The plasmid pFoldon which had been previously shown to express the bacteriophage T4 fibritin foldon domain in 293T cells was constructed by inserting the PCR-amplified gene fragment into the pCDA3.1-V5-His-TOPO vector (Invitrogen, Carlsbad, Calif.). pFoldonTGA, which encodes the Trp68TGA foldon mutant, was constructed by site-directed mutagenesis of pFoldon using the QuikchangeXL method and the corresponding HPLC-purified primers.

Expression and Detection of Mu tRNA$_{UCA}^{Trp}$ in Mammalian Cells.

Mammalian 293T cells were transfected with plasmid pTrptRNA and incubated at 37° C. under 5% $CO_2$ for 60 hours. Cellular RNA was extracted with TRIZOL solution according to manufacturer's instructions (Invitrogen) and the total tRNA was then isolated using a NucleoBond column according to manufacturer's protocol (Clontech). The yield and purity of the purified tRNA were analyzed with a 3% agarose gel. To detect the mu tRNA$_{UCA}^{Trp}$, the purified tRNAs were first blotted and then cross-linked onto nylon transfer membranes (Osmonics, Westborough, Mass.) by UV irradiation using Stratalinker 2400 (Stratagene) for 1 min. Following irradiation, the membrane was incubated in 100 ml of hybridization buffer (0.9 M NaCl, 0.09 M sodium citrate, pH 7.0, 1% SDS, 5×Denhardt's reagent with 25 µg/ml sperm whale DNA) and gently shaken at 68° C. for 1 hour. The oligonucleotide, CGGAGGTTTTGAAGACCTCTGCT (SEQ ID NO:7), which is complementary to nucleotides 27 to 44 of the suppressor tRNA, was 5'-labeled with [$\gamma$-$^{32}$P]ATP and used to probe the membrane at 50° C. for 6 hours. The membrane was then washed three times with wash buffer (15 mM NaCl, 1.5 mM sodium, pH 7.0, 0.1% SDS). The intensity of each dot was quantified using a PhosphorImager (Molecular Dynamics).

Expression of *B. subtilis* TrpRS in Mammalian 293T Cells.

Cells were transfected with the plasmid pEF6-TrpRS and incubated at 37° C. under 5% $CO_2$ for 60 hours. Cells were harvested and lysed with 1× passive lysis buffer (Promega, Madison, Wis.), and the cell lysate was centrifuged at 20,000×g. Proteins were separated by denaturing SDS-polyacrylamide gel electrophoresis and then transferred to a nitrocellulose membrane for Western blot analysis. Proteins were probed with primary anti-His6 antibody followed by secondary horseradish peroxidase-conjugated goat anti-rabbit IgG. Substrate (SuperSignal West Dura, Pierce) was applied to visualize the signals.

In Vitro Aminoacylation Assay.

Aminoacylation assays were performed essentially as described in Methods in Enzymology 113, pp. 55-59, by Hoben, P. & Soll, D., (1985), to evaluate RSs and tRNAs of the invention. 20 µL reactions prepared containing 50 mM Tris-HCl, pH 7.5, 30 mM KCl, 20 mM $MgCl_2$, 3 mM glutathione, 0.1 mg/ml BSA, 10 mM ATP, 1 µM (33 Ci/mM) L-[5-$^3$H]-tryptophan, 750 nM synthetase, and 20 µM purified total tRNA. Assays were carried out to 10% conversion.

Opal Suppression in Mammalian Cells.

Transfections were carried out with Fugene 6 using a total of 2 µg DNA per 9.5 $cm^2$ plate according to the manufacturer's protocol (Roche). Minimum essential alpha medium (Gibco BRL) was used as the growth medium. Cell extracts were prepared 48 hours after transfection and subjected to SDS-polyacrylamide gel electrophoresis, followed by Western blot analysis using anti-V5 antibody (Invitrogen) and the SuperSignal West Dura immunodetection system (Pierce). The signals were detected by exposing the membrane to Hyperfilm MP (Amersham Pharmacia).

Unnatural Amino Acid Incorporation in Mammalian Cells.

Mammalian 293T cells were co-transfected with individual plasmids pTrptRNA, pFoldonTGA and mutant pEF6-TrpRS (i.e., pVal144ProBsTrpRS), as previously described.

After 24 hours, the culture medium was changed to minimum essential alpha medium containing 1 mM 5-hydroxy-L-tryptophan and appropriate antibiotics. After an additional 48 hours at 37° C. under 5% $CO_2$, cells were harvested, lysed with 1× passive lysis buffer (Promega, Madison, Wis.), and the cell lysate was collected by centrifugation at 20,000×g. The foldon protein containing 5-hydroxy-L-tryptophan was purified from the cell lysate (twenty 50 ml culture plates) with Ni-NTA beads followed by anti-V5-immobilized agarose beads according to manufacturer's protocol (Bethyl Laboratories, Montgomery, Tex.). An aliquot of the purified protein was subjected to high resolution electrospray ionization mass spectrometry.

Fluorescence Spectroscopy.

Proteins were diluted to a final concentration of 50 nM in 10 mM $K_2PO_4$, 100 mM KCl buffer at pH 7.5. Fluorescence spectra were measured on a Fluromax-2 spectrofluorimeter and corrected. Excitation spectra were recorded with an excitation bandpass of 4 nm and an emission bandpass of 8 nm; emission spectra were recorded with emission bandpass of 4 nm.

Electrochemical Characterization of Proteins Containing 5-hydroxy-L-tryptophan.

A conventional three-electrode cell, consisting of a gold electrode, a glassy carbon auxiliary electrode isolated by a glass frit, and a saturated calomel electrode (SCE) connected to the working volume with a Luggin capillary, was used for electrochemical measurements. The cell was placed in a grounded Faraday cage. Cyclic voltammetry measurements were performed using a potentiostat (Princeton Applied Research, model VMP2, Oak Ridge, Tenn.) connected to network operated software EC-Lab v6.61. All electrochemical measurements were performed in 0.1 M phosphate buffer, pH 7.4 under argon atmosphere. Substrate 5-HTPP was dissolved in 100 mM phosphate buffer to a final concentration of 10 μg/mL. Potentials were measured in the range of 0-800 mV at a scan rate of 1 V·$sec^{-1}$. For cross-linking experiments, the electrode potential was set to 800 mV for 30 minutes in the presence of 10 μg/mL wild type foldon or 5-HTPP-foldon protein, 0.1 M phosphate buffer, pH 7.4 under argon atmosphere. After that, the solutions were collected, proteins were desalted by dialysis, concentrated and loaded on a gel for further analysis.

Results and Discussion

An Orthogonal Opal Suppressor tRNA for Use in Mammalian Cells.

To genetically encode an unnatural amino acid in mammalian cells, we generated an orthogonal tRNA (O-tRNA) which is not recognized by any of the aminoacyl tRNA synthetases in the mammalian endogenous translation system, yet which efficiently incorporates its cognate amino acid in response to a unique codon, in this case the opal nonsense codon TGA. A corresponding (paired complimentary) orthogonal aminoacyl-tRNA synthetase (O-RS) was provided which uniquely recognizes the O-tRNA and selectively (preferentially) charges it with the unnatural amino acid, and not with endogenous amino acids. Generation of the O-RS/O-tRNA orthogonal pair took advantage of inter-species differences in tRNA recognition elements. For example, it has been shown that *B. subtilis* $tRNA^{Trp}$ is generally not a substrate for the tryptophan-tRNA synthetases from yeast and mammalian cells. In addition, kinetic studies of others have demonstrated that mutation of the anticodon loop of this tRNA has only a minor effect (<5%) on aminoacylation by the cognate *B. subtilis* TrpRS. Thus, *B. subtilis* $tRNA^{Trp}$ was a good candidate for development of an orthogonal suppressor tRNA in the mammalian cells.

However, to our surprise, *B. subtilis* $tRNA^{Trp}$ was not detected by northern blot analysis of isolated total tRNA from 293T cells transfected with the sequence. Therefore, a series of modifications were made to the *B. subtilis* suppressor $tRNA^{Trp}$ sequence (see, FIG. 1). Transfer RNAs in eukaryotes are transcribed by RNA polymerase III which recognizes two conserved intragenic transcriptional control elements, the A box and the B box. Since the *B. subtilis* $tRNA^{Trp}$ sequence contains only the B box, nucleotides A7, A9, U11 were changed to G7, G9 and C11, respectively, in order to generate a pseudo A box. To retain proper arm structure, the resulting mismatched base pairs G7-U64 and C11-A23 were replaced with G7-C64 and C11-G23, respectively. Expression of the $tRNA^{Trp}$ gene in eukaryotes is known to depend upon 5' flanking sequences which are distinctly AT rich and contain several possible TATA elements. Therefore, a 5' flanking sequence was added from the $tRNA^{Trp1}$ gene from *Arabidopsis* (Trp1), which was previously shown to enhance the transcription of the plant $tRNA^{Trp}$ gene in human 293T cells. Since a properly positioned terminator element is the only 3' flanking sequence required for efficient expression of the plant $tRNA^{Trp}$ gene, the natural 3' flanking sequence of the same $tRNA^{Trp1}$ gene was used. Finally, the trinucleotide anticodon sequence CCA was changed to the opal suppressor UCA (C33U).

Figure 2A:
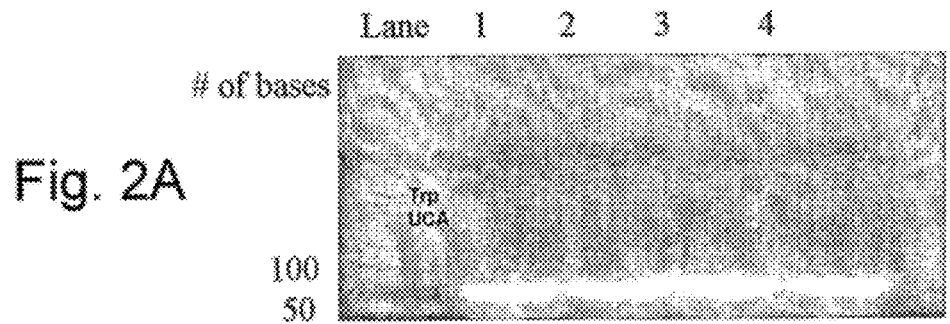
FIG. 2A shows a 3% agarose gel electrophoresis of purified total tRNA isolated from: E. coli (lane 1), beef liver (lane 2), 293T cells (lane 3), and 293T cells transfected with pTrptRNA plasmid (lane 4).
Figure 2B:
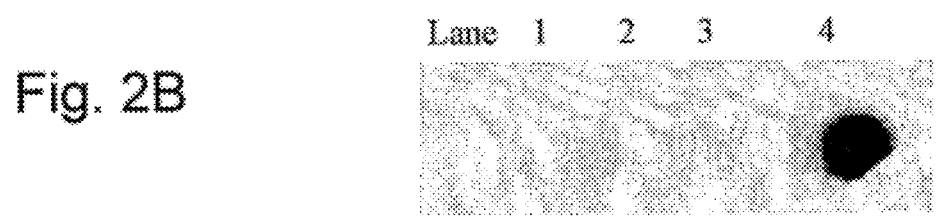
FIG. 2B shows dot blots of purified total tRNAs from E. coli (lane 1), beef liver (lane 2), 293T cells (lane 3), and 293T cells transfected with pTrp-tRNA plasmid (lane 4) blotted onto a membrane separately and probed with a 5'-$^{32}$P-labeled oligonucleotide complementary to nucleotides 27 to 44 of the mutRNA$_{UCA}^{Trp}$.

The expression of the modified opal suppressor $tRNA^{Trp}$ ($mutRNA_{UCA}^{Trp}$) was verified using a Northern blot assay. The mutant $tRNA_{UCA}^{Trp}$ gene together with its 5' and 3' flanking sequences were cloned into the mammalian vector pZeoSV2(+) and the resulting plasmid was transfected into human 293T cells using Fugene 6. Total tRNA was then isolated and blotted onto a membrane. As a control, the same amount of total tRNA from human 293T cells, beef liver, and *E. coli* were also transferred onto the same membrane (FIG. 2A). A synthetic oligonucleotide complementary to nucleotides 27 to 44 of the $mutRNA_{UCA}^{Trp}$ and labeled with [γ-$^{32}$P] ATP was used as a probe for the mu $tRNA_{UCA}^{Trp}$. Only the total tRNA isolated from transfected 293T cells produced a signal (lane 4, FIG. 2B); the control tRNAs gave no signal when incubated with the radioactive oligonucleotide probe (lane 1-3, FIG. 2B). These results demonstrated that the $mutRNA_{UCA}^{Trp}$ is expressed in mammalian cells.

BsTrpRS is an Orthogonal Synthetase in Mammalian Cells.

Given the availability of an orthogonal mammalian suppressor tRNA, we next examined whether the corresponding BsTrpRS can efficiently aminoacylate the $mutRNA_{UCA}^{Trp}$ and not the endogenous mammalian tRNAs. To determine the efficiency of aminoacylation of $mutRNA_{UCA}^{Trp}$ by BsTrpRS, in vitro aminoacylation assays were carried out with BsTrpRS purified from *E. coli*. Plasmid pMHTrpRS was used to express BsTrpRS with an N-terminal His6 purification tag, under control of an L-arabinose promoter. BsTrpRS was purified by Ni-NTA affinity chromatography with a yield of 5 mg/L. In vitro aminoacylation assays were then performed with $^3$H-labeled tryptophan and various total tRNAs. BsTrpRS was found to efficiently charge the total tRNA isolated from *B. subtilis* cells containing cognate *B. subtilis* $tRNA^{Trp}$. In agreement with the published data, BsTrpRS did not aminoacylate total mammalian tRNA isolated from 293T cells at detectable levels. However, total tRNA isolated from transfected 293T cells expressing mu $tRNA_{UCA}^{Trp}$ was efficiently charged with $^3$H-tryptophan by BsTrpRS. The overall aminoacylation activity of BsTrpRS for $mutRNA_{UCA}^{Trp}$ in mammalian total tRNA was about 40% of that for *B. subtilis* tRNA$^{Trp}$ in total bacterial tRNA, possibly due to a lower expression level of mutRNA$_{UCA}^{Trp}$ in mammalian cells. Nevertheless, this experiment indicated that BsTrpRS can efficiently charge mutRNA$_{UCA}^{Trp}$, and, importantly, does not aminoacylate endogenous mammalian tRNAs to any appreciable extent.

BsTrpRS was expressed in mammalian cells using plasmid pEF6-TrpRS, which carries the BsTrpRS gene with a C-terminal His6 tag under the control of the human promoter EF-1α. Mammalian 293T cells were transiently transfected with plasmid pEF6-TrpRS using Fugene 6. Protein from the cell lysate was separated by SDS-PAGE, and subjected to Western blot analysis using an anti-C-terminal V5 antibody probe. A band corresponding to the full length prokaryotic BsTrpRS protein (~36 kDa) was observed, demonstrating that the synthetase can be expressed in mammalian cells at usable levels (lane 1, FIG. 4). No significant effect on growth rates was observed upon expression of the exogenous B. subtilis TrpRS.

Opal Suppression in 293T Cells is Dependent on the Expression of the BsTrpRS-Mu tRNA$_{UCA}^{Trp}$ Orthogonal Pair.

The ability of the mutRNA$_{UCA}^{Trp}$-BsTrpRS orthogonal pair to efficiently suppress an opal mutation in mammalian cells was determined. A construct of bacteriophage T4 fibritin foldon was mutated at the codon for Trp68 to the opal codon (TGA) to provide a suppressor test substrate. Based on previous data, mutation of Trp68, which is located in the interior of the foldon protein, to a tryptophan analogue was unlikely to disrupt the structure of this protein. To detect the expression of the full-length foldon protein, a V5 epitope detectable maker tag and a His6 purification tag were fused to the C-termini of the wild type (pFoldonWT) and mutant foldon proteins (pFoldonTGA) by recombinant DNA technology. These foldon expression constructs were transfected into human 293T cells along with either one or both of the BsTrpRS and mutRNA$_{UCA}^{Trp}$ constructs. Any expressed full length protein was detected by anti-V5 antibody western blot analysis of the cell extracts.

Figure 3:
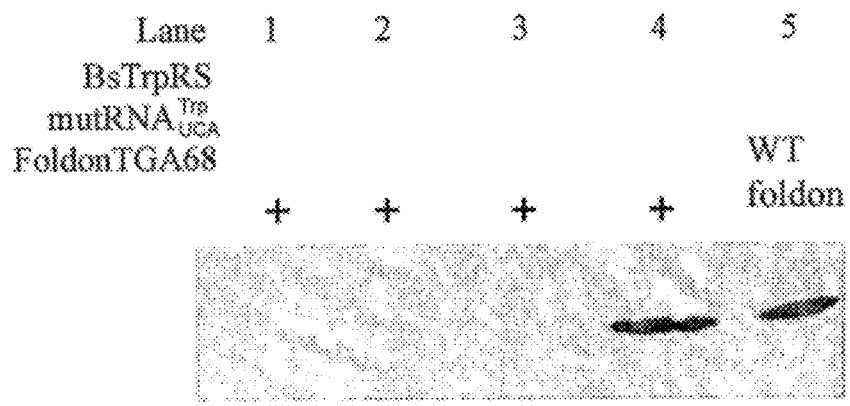
FIG. 3 shows Western blot analysis for detection of opal suppression in 293T cells. A lysate from a TGA68foldon construct transfection is shown in lane 1 of the blot. A lysate from a wild type foldon construct transfection is shown in lane 5 as a positive control. In the absence of either opal suppressor tRNA$^{Trp}$ (lane 2) or BsTrpRS (lane 3), no full-length protein was expressed as detected by Western blot with anti-V5 antibody. In the presence of both opal suppressor tRNA$^{Trp}$ and BsTrpRS, the opal codon in the TGA68foldon construct was suppressed and the full-length foldon protein was expressed (lane 4).

No full-length protein was expressed when 293T cells were transfected with only the mutant foldon construct (pFoldonTGA) (lane 1, FIG. 3), or with the mutant foldon construct in combination with the wild type BsTrpRS (lane 2, FIG. 3). These results showed that human 293T cells do not contain intrinsic opal suppressor tRNAs for the TGA68 mutation. In addition, suppression of the opal mutation was not observed in the presence of mutRNA$_{UCA}^{Trp}$ but without wild type BsTrpRS (lane 3, FIG. 3), confirming that the mutRNA$_{UCA}^{Trp}$ is not charged by endogenous synthetases in human 293T cells. In contrast, in the presence of the mutRNA$_{UCA}^{Trp}$, wild type BsTrpRS, and TGA68 mutant foldon gene, expression of the full-length protein was detected (lane 4, FIG. 3). For comparison, lane 5 shows the expression of wild type (wt) foldon protein in 293T cells. Based on integration of the western blot signals for lanes 4 and 5, the suppression efficiency is approximately 38%. These experiments, together with the above in vitro aminoacylation assays, showed that BsTrpRS aminoacylates only mutRNA$_{UCA}^{Trp}$ and not other endogenous mammalian tRNAs, and that the expressed mutRNA$_{UCA}^{Trp}$ is charged only by its cognate BsTrpRS and not by other endogenous mammalian synthetases. Thus, B. subtilis TrpRS-mutRNA$_{UCA}^{Trp}$ represents an orthogonal pair that functions in mammalian cells and translation systems.

The suppression efficiency of this homologous pair of tRNA$^{Trp}$-TrpRS (both derived from Bacillus subtilis) is significantly higher than that of the reported heterologous pair (K. Sakamoto, et al., N. A. Res., Vol. 30, No. 21 4692-4699, (2002)) of B. stear. tRNA$^{Tyr}$-E.c.TyrRS in mammalian cells, and similar to the efficiencies reported for the human suppressor tRNA$^{Tyr}$ and other suppressor tRNAs functioning in mammalian cells (20-40%). Sakamoto et al. showed that a construct with a gene cluster of nine suppressor tRNA copies can significantly increase suppression efficiency in mammalian cells. However, this method was not employed in this Example since a single copy of the mutRNA$_{UCA}^{Trp}$ gene was sufficient to suppress the TGA68 codon for production of full-length protein at a level detectable by western blot analysis (≥10 pg/cell). In addition, toxicity observed at higher levels of transfection (4 μg versus 2 μg plasmid pTrptRNA/10$^6$ cells) indicated multicopy suppression may be undesirable in the case of these mutRNA$_{UCA}^{Trp}$ constructs in 293T cells.

Site-Specific Incorporation of 5-hydroxy-L-tryptophan (5-HTPP) into Mammalian Cells.

We next asked whether the orthogonal mutRNA$_{UCA}^{Trp}$-BsTrpRS pair could be used to selectively incorporate 5-hydroxy-tryptophan (5-HTPP) into proteins in mammalian cells in response to the opal nonsense codon. This amino acid has unique spectroscopic and redox properties that can serve, e.g., as useful probes of protein structure and function both in vitro and in vivo. It is known that wild type B. subtilis TrpRS does not utilize 5-HTTP as a substrate. Therefore, in order to use BsTrpRS to selectively incorporate 5-HTPP into proteins, the active site of the synthetase was be mutated to charge 5-HTPP and not tryptophan. Although the structure of BsTrpRS was not available for protein engineering in this case, the structure of a highly homologous tryptophanyl-tRNA synthetase from the analogous Bacillus stearothermophilus translation system had been solved to 1.9 Å resolution. The active site of this enzyme has a figure eight like shape with two adjacent binding pockets separated by an α-helix peptide consisting of residues Asp140, Ile141, Val142, Pro143, Val144, and Gly145. Val144 points directly towards C5 of tryptophan, appearing to provide unfavorable steric interactions with any tryptophan analogue having additional substituent chemical groups at the 5 position. Mutation of Val144 to a smaller amino acid was logically identified as an approach to provide space for 5-substituted tryptophan analogues.

Figure 4:
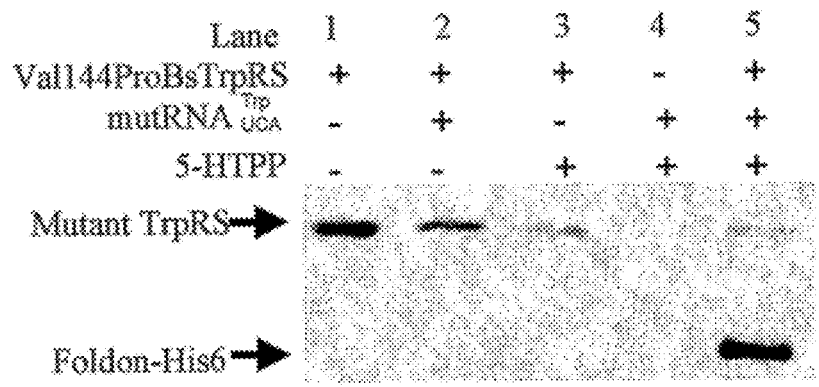
FIG. 4 shows a Western blot indicating incorporation of 5-HTPP into foldon protein in 293T cells. The wild type BsTrpRS with a V5 tag was expressed in 293T cells (lane 1). In the absence of either 5-HTPP, mutRNA$_{UCA}^{Trp}$, or Val144ProBsTrpRS, no full-length protein was translated (lanes 2-4) for the TGA68foldon construct. In the presence of 5-HTPP, Val144ProBsTrpRS and mutRNA$_{UCA}^{Trp}$, the full-length opal mutant foldon protein was expressed as detected by western analysis with anti-V5 antibody (lane 5).

To test this notion, Val144 of wild type BsTrpRS was mutated to each of the other nineteen amino acids by site-directed mutagenesis and the mutants were screened for an ability to aminoacylate the mutRNA$_{UCA}^{Trp}$ with 5-HTPP for suppression of the TGA68 in the mutant foldon construct. The transfected cells were then grown in the presence or absence of 1 mM 5-HTPP, and full-length protein was detected by Western blot of the cell extracts with an anti-V5 antibody (FIG. 4). Theoretically, expression of a full-length foldon protein in the presence of 5-HTPP would indicate that either 5-HTPP or a natural amino acid (likely tryptophan) is incorporated at position 68 of the foldon protein. The natural amino acid incorporation alternative could be excluded by showing that no full length protein is expressed in the absence of 5-HTPP under otherwise the same conditions. In this example, among the 19 TrpRS mutants, the Val144Gly mutant was able to suppress the TGA68 codon in the presence of 1 mM 5-HTPP and mutRNA$_{UCA}^{Trp}$. However, in the absence of 5-HTPP, the mutant BsTrpRS and mu tRNA$_{UCA}^{Trp}$ were still able to suppress the opal mutation, indicating the Val144GlyBsTrpRS mutant also charges a natural amino acid. Only one other TrpRS mutant, Val144ProBsTrpRS, was able to suppress the TGA68 mutation in the presence of 1 mM 5-HTPP and mutRNA$_{UCA}^{Trp}$ (lane 5, FIG. 4). Moreover, human 293T cells containing the Val144ProBSTrpRS and the TGA68 foldon gene were unable to produce full-length protein in the absence of either 5-HTPP or mutRNA$_{UCA}^{Trp}$ (lane 2-4, FIG. 4). These results showed that the Val144ProBsTrpRS mutant selectively aminoacylates the mutRNA$_{UCA}^{Trp}$ with 5-HTPP, and not with any endogenous natural amino acids. The yield of the HTPP68 mutant protein was approximately 100 µg/liter of culture, compared to that of about 1 mg/liter for wt protein, providing about 10% of native activity in culture media containing 1 mM 5-HTPP.

In order to confirm that the expressed mutant protein contains 5-HTPP, the protein was purified first by Ni-NTA affinity chromatography and, subsequently, by immuno-precipitation using anti-V5-immobilized agarose beads. An aliquot of the purified protein was subjected to high resolution electrospray ionization (ESI) mass spectrometry. The calculated molecular weight of the HTPP68 mutant protein is 14323.6 Da; the observed molecular weight was 14323.69 Da. No peak corresponding to wild type foldon protein was observed. This result demonstrated that 5-HTPP is incorporated with high fidelity (>97%) into protein in response to the opal codon in mammalian cells.

Characterization of Orthogonal Aminoacylation Activity.

The Val144ProBsTrpRS mutant was found to selectively aminoacylate the mutRNA$_{UCA}^{Trp}$ with 5-HTPP at an activity similar to many endogenous RS/tRNA pairs. For example, the orthogonal pair was selective in that activity with natural tryptophan substrate was undetected while the Michaelis constant ($K_m$) for 5-hydroxytryptophan substrate and the catalytic rate constant ($k_{cat}$) for 5-HTPP were in a range not atypical of endogenous components. These Val144ProBsTrpRS-mutRNA$_{UCA}^{Trp}$ pair demonstrated at least a 33-fold selectivity of the orthogonal pair for 5-HTPP over natural tryptophan in the translation system. Such catalytic activity is comparable to the activity of many endogenous RS/tRNA pairs for their natural amino acid substrate.

Figure 5:
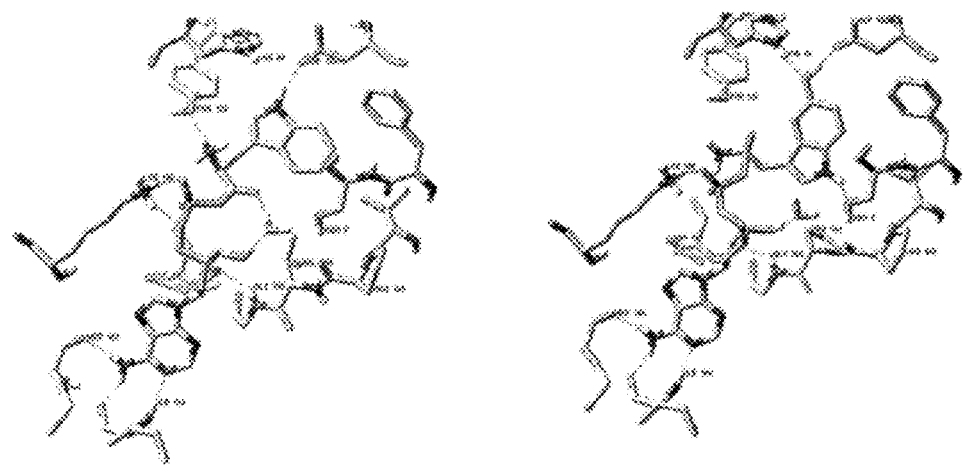
FIG. 5 shows a computational simulation of a complex between TrpRS and its substrates using Macromodel (Version 8.1, Schrodinger, LLC.). Hydrogen bonds are indicated as dotted lines (-------) The left structure illustrates the binding of wt B. subtilis TrpRS with its cognate substrate, tryptophan-5'AMP, including the hydrogen bond between the indole NH group and Asp133. The right structure illustrates the complex between the Val144ProBsTrpRS and its substrate, 5-HTPP-5'AMP. Note the disappearance of the hydrogen bond between the indole NH group and Asp 133, and the new hydrogen bonds between the 5-OH and His44, Asp133, and the indole NH and Ser7.

It was somewhat surprising that a single mutation at the active site of BsTrpRS completely altered its specificity from L-tryptophan to 5-HTPP. This specificity was investigated by computer-assisted modeling (Macromodel version 8.1, Schrodinger, LLC.) suggesting that the Val144Pro mutation generated space for the indole ring to rotate and abolished an indole NH-Asp hydrogen bond. This can explain why the Val144ProBsTrpRS does not charge L-tryptophan. However, new hydrogen bonds are formed in the case of 5-HTPP with the 5-OH group hydrogen bonding with the imidazole side chain of His44 and the carboxylate group of Asp133, and the indole NH hydrogen bonding with the hydroxyl group of Ser7 (as shown in FIG. 5). Libraries of BsTrpRS (and other RS) variants with several other sites randomly mutated, can be similarly investigated using computer models and/or screened in the laboratory to identify mutants that selectively recognize additional side chain structures.

5-HTPP as a Probe for Protein Structure and Function.

Figure 6:
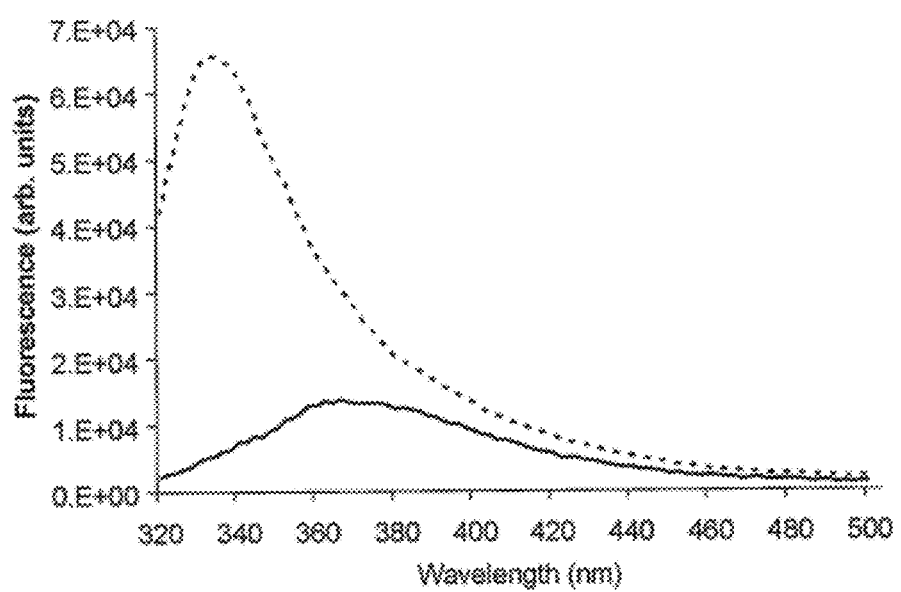
FIG. 6 shows a fluorescence spectra of wt foldon protein (———) and the HTPP68 mutant protein (••••••) with excitation at 310 nm.

5-Hydroxy-L-tryptophan has significant absorbance at 310 nm at pH 7.5 ($\epsilon$=2450 M$^{-1}$cm$^{-1}$), compared to that of tryptophan ($\epsilon$=62 M$^{-1}$cm$^{-1}$) at 310 nm, suggesting 5-HTPP can be a useful spectroscopic probe in proteins. Wild type foldon protein has only one tryptophan residue, which is substituted in the mutant foldon protein with 5-HTPP. To compare the fluorescence properties of these two proteins, they were purified and then excited at 310 nm at pH 7.4 for recordation of their emission spectra (see, FIG. 6). The HTPP68 foldon protein has an emission maximum, $\lambda_{max}$, at 334 nm (dotted line), while the wild type foldon protein has a fluorescence $\lambda_{max}$ at 367 nm (solid line). When both proteins were excited at 310 nm, the magnitude of fluorescence emission at 334 nm from HTPP68foldon protein was 11 times higher than for the wild type foldon protein. Such spectral shifts can make 5-HTPP a useful optical probe for some applications.

5-HTPP can also undergo redox chemistry to afford tryptophan-4,5-dione. Cyclic voltammetry was used to determine whether the redox wave of 5-HTPP could be observed in the HTPP68foldon mutant. The voltammetric responses were measured for solutions containing 10 µM of HTPP, wt foldon, or the foldon mutant. An anodic current originating from HTPP oxidation appeared only in the presence of the mutant foldon or in a solution of free 5-HTPP with E=400 mV and E=450 mV, respectively, indicating the presence of 5-HTPP in the mutant foldon. The slight decrease in the oxidation potential for the mutant protein possibly resulted from differential stabilization of the oxidized and reduced forms of 5-HTPP in aqueous solution versus the hydrophobic protein core. No current was observed upon attempts to oxidize the wild type foldon.

Figure 7A:
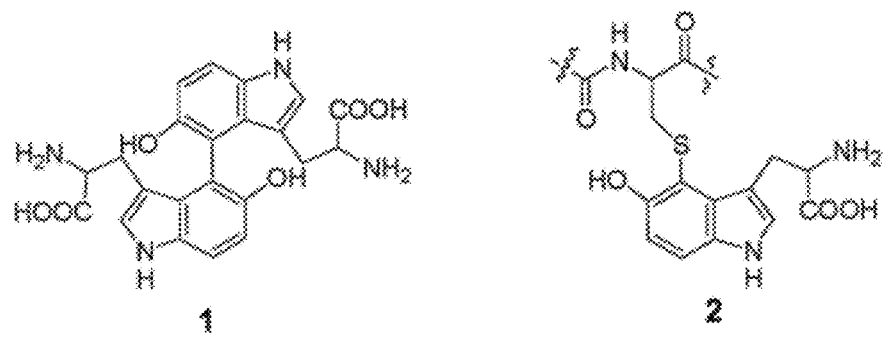
Figure 7B:
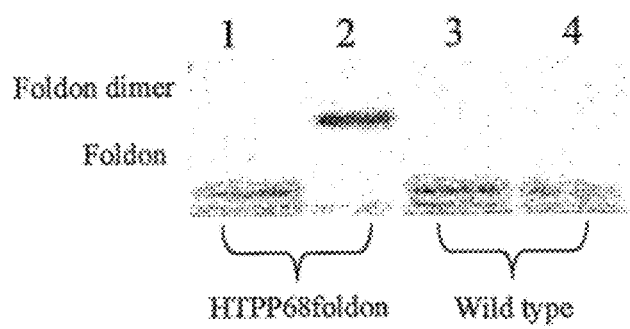
FIG. 7B shows an SDS-PAGE analyses of proteins oxidatively cross-linked with 5-HTPP. The proteins were separated with 4-20% gradient SDS-PAGE and Coommassie-stained. Lane 1 and lane 3 contain the purified HTPP68foldon and wild type foldon proteins, respectively. Lane 2 contains the cross-linking product for HTPP68 foldon, and lane 4 contains the cross-linking product for wild type foldon protein. There was no detectable cross-linked product for wild type foldon which has a monomeric molecular weight of 14.5 kDa. HTPP68foldon was cross-linked to afford a dimeric 29 kDa protein.

Upon electrochemical oxidation of 5-HTPP at a potential 800 mV in 7.4 phosphate buffer, the dimer (1, FIG. 7A) was formed. Similarly, 5-HTPP can be oxidatively cross-linked to glutathione via its cysteine residue (2, FIG. 7A). Therefore a 5-HTPP residue incorporated selectively into a protein can be useful as a redox cross-linker. In order to test this notion, we attempted to cross-link the HTPP68foldon mutant electrochemically by applying a positive potential of 800 mV to the working electrode in a solution containing either the HTPP68foldon protein or wild type foldon for 30 minutes in phosphate buffer. The resulting proteins were desalted, concentrated, denatured, and separated using 4-20% gradient denaturing SDS-PAGE. The resulting gel was Coommassie-stained (FIG. 7B). Lane 1 is the full-length HTPP68foldon mutant with a molecular weight of 14.5 kDa. Lane 3 is wild type foldon protein with the same apparent molecular mass. Lane 2 is the electrochemically oxidized product of the HTPP68foldon protein, which has a molecular weight of about 29 kDa, and corresponds to the dimeric mutant foldon protein. The yield was estimated to be 80% as determined from band intensities. In contrast, there is no cross-linked product in lane 4 which contains the wild type foldon protein under the same conditions. This result showed protein cross-linking HTPP68foldon alloprotein through the incorporated 5-HTPP.

While the foregoing invention has been described in some detail for purposes of clarity and understanding, it will be apparent to one skilled in the art from a reading of this disclosure that various changes in form and detail can be made without departing from the true scope of the invention. For example, many of the techniques and constructs described above can be used in various combinations, or with alternate mutants or substrates.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of reacting a peptide comprising a 5-hydroxy-L-tryptophan (5-HTPP) with a molecule reactive with 5-HTPP, the method comprising:
providing a peptide comprising one or more unnatural amino acids wherein at least one of the unnatural amino acids is 5-hydroxy-L-tryptophan (5-HTPP),
providing a reactive molecule reactive with the 5-HTPP; and,
reacting the reactive molecule covalently with the 5-HTPP, wherein said providing the peptide comprises:
  i) preparing a construct comprising a nucleic acid sequence encoding an orthogonal tRNA synthetase (O-RS) and comprising at least 90% identity to the sequence of SEQ ID NO: 2, the O-RS comprising a proline residue at a position corresponding to position 144 of SEQ ID NO: 2, wherein the O-RS aminoacylates a reference orthogonal tRNA (O-tRNA) of SEQ ID NO: 3 with a 5-HTPP when the reference O-tRNA, 5-HTPP, and the O-RS are present in a eukaryotic cell;
  ii) preparing a construct comprising a nucleic acid sequence encoding an O-tRNA comprising: at least 90% identity to SEQ ID NO: 3, wherein the O-tRNA is aminoacylated with a 5-HTPP by a reference O-RS of SEQ ID NO: 2 when the reference O-RS, 5-HTPP, and the O-tRNA are present in a eukaryotic cell;
  iii) introducing the O-RS construct and the O-tRNA construct into the eukaryotic cell; and,
  iv) preferentially aminoacylating an expressed O-tRNA with the 5-HTPP, wherein said aminoacylation is catalyzed by an expressed O-RS, wherein the O-tRNA recognizes a selector codon in a nucleic acid sequence encoding the peptide, whereby the 5-HTPP is incorporated into the peptide in the eukaryotic cell.

2. The method of claim 1, further comprising applying a voltage to the peptide, thereby reacting the 5-HTPP with the reactive molecule.

3. The method of claim 1, wherein reacting comprises cross-linking.

4. The method of claim 1, wherein the reactive molecule comprises an unnatural amino acid in another peptide.

5. The method of claim 4, wherein the amino acid on another peptide is selected from the group consisting of: 5-HTPP and cysteine.

6. The method of claim 1, further comprising detecting an interaction between the peptide and another peptide.

7. The method of claim 6, wherein said detecting comprises fluoroscopy.

* * * * *